US012622875B2

(12) United States Patent
Haksar et al.

(10) Patent No.: US 12,622,875 B2
(45) Date of Patent: *May 12, 2026

---

(54) DOSAGE FORM COMPRISING AN ALKALINE AGENT AND AN ENTERIC COATING LAYER

(71) Applicant: Evonik Operations GmbH, Essen (DE)

(72) Inventors: Priyanka Haksar, Thane (IN); Shraddha Joshi, Thane (IN); Umesh Kapale, Solapur (IN); Nilam Bharambe, Dombivali West (IN); Ashish Guha, Mumbai (IN); Vinay Jain, Mumbai (IN)

(73) Assignee: Evonik Operations GmbH, Essen (DE)

( * ) Notice: Subject to any disclaimer, the term of this patent is extended or adjusted under 35 U.S.C. 154(b) by 896 days.

This patent is subject to a terminal disclaimer.

(21) Appl. No.: 17/757,060

(22) PCT Filed: Sep. 17, 2020

(86) PCT No.: PCT/EP2020/075960
§ 371 (c)(1),
(2) Date: Jun. 8, 2022

(87) PCT Pub. No.: WO2021/115648
PCT Pub. Date: Jun. 17, 2021

(65) Prior Publication Data
US 2023/0000780 A1      Jan. 5, 2023

(30) Foreign Application Priority Data
Dec. 11, 2019    (IN) .............................. 201941051238

(51) Int. Cl.
| | |
|---|---|
| *A61K 9/28* | (2006.01) |
| *A61K 31/18* | (2006.01) |
| *A61K 31/4439* | (2006.01) |
| *A61K 31/55* | (2006.01) |

(52) U.S. Cl.
CPC .......... *A61K 9/2886* (2013.01); *A61K 9/2813* (2013.01); *A61K 9/2846* (2013.01); *A61K 9/2866* (2013.01); *A61K 31/18* (2013.01); *A61K 31/4439* (2013.01); *A61K 31/55* (2013.01)

(58) Field of Classification Search
None
See application file for complete search history.

(56) References Cited

U.S. PATENT DOCUMENTS

| | | |
|---|---|---|
| 4,786,505 A | 11/1988 | Lovgren et al. |
| 7,871,643 B2 | 1/2011 | Lizio et al. |
| 7,932,258 B2 | 4/2011 | Petereit et al. |

| | | | |
|---|---|---|---|
| 11,730,708 B2 * | 8/2023 | Haksar ................. | A61K 9/2054 |
| | | | 424/480 |
| 2002/0098232 A1 | 7/2002 | Midha et al. | |
| 2005/0214371 A1 | 9/2005 | Di Capua et al. | |
| 2007/0065513 A1 * | 3/2007 | Avramoff ............. | A61K 9/5078 |
| | | | 424/470 |
| 2009/0028941 A1 * | 1/2009 | Cowles ................. | A61K 9/4808 |
| | | | 514/338 |
| 2010/0129446 A1 * | 5/2010 | Liu ....................... | A61K 9/5073 |
| | | | 514/263.34 |
| 2010/0255092 A1 | 10/2010 | Ravishankar et al. | |
| 2013/0266658 A1 | 10/2013 | Weiß et al. | |
| 2016/0022590 A1 * | 1/2016 | Odidi ................... | A61K 9/2886 |
| | | | 424/463 |
| 2016/0081933 A1 | 3/2016 | Hensel et al. | |
| 2016/0193182 A1 | 7/2016 | Joshi et al. | |
| 2022/0241155 A1 | 8/2022 | Jain et al. | |
| 2023/0012981 A1 | 1/2023 | Haksar et al. | |
| 2023/0048354 A1 * | 2/2023 | Haksar ................. | A61K 9/5047 |

FOREIGN PATENT DOCUMENTS

| | | |
|---|---|---|
| CN | 102626398 | 8/2012 |
| CN | 102626398 A | 8/2012 |
| CN | 105640915 A | 6/2016 |
| EP | 3 388 056 | 10/2018 |
| GB | 2 189 698 | 11/1987 |

(Continued)

OTHER PUBLICATIONS

Extended European Search Report issued Jul. 8, 2020 in European Patent Application No. 20153758.6, 7 pages.
International Search Report issued Dec. 17, 2020 in PCT/EP2020/075960, 6 pages.
Written Opinion issued Dec. 17, 2020 in PCT/EP2020/075960, 7 pages.
Anonymous, "Stabilized Pharmaceutical Formulation", iP.com, Prior Art Database, Sep. 17, 2002, XP002374253, 3 pages.
Extended European Search Report dated Jul. 10, 2020, in European Application No. 20153812.1, 8 pages.
Extended European Search Report dated Jul. 13, 2020, in European Application No. 20153822.0, 8 pages.

(Continued)

*Primary Examiner* — Danah Al-Awadi
(74) *Attorney, Agent, or Firm* — Grüneberg Global IP, PLLC

(57) ABSTRACT

A dosage form contains a) a core, containing a biologically active ingredient, which is stable to a degree of at least 95% at a pH of 3 for 2 hours at 22° C.; b) an intermediate coating layer (ICL) onto or above the core, containing an alkaline agent; and c) an enteric coating layer (ECL) onto or above the intermediate coating layer, containing an enteric polymer. The relation in percent of the alkaline agent in the ICL to the enteric polymer in the ECL is 5 to 95% when calculated by the formula:

$$\frac{\text{quantity of alkaline agent in grams in the } ICL \times 100}{\begin{array}{c}(\text{quantity of alkaline agent in grams in the } ICL + \\ \text{quantity of enteric polymer in grams in the } ECL).\end{array}}$$

19 Claims, No Drawings

(56)                References Cited

FOREIGN PATENT DOCUMENTS

| JP | 62-258320 | 11/1987 |
| JP | 62-258320 A | 11/1987 |
| JP | 2009-544639 | 12/2009 |
| JP | 2009-544639 A | 12/2009 |
| WO | 2005/092297 | 10/2005 |
| WO | 2008/135090 | 11/2008 |
| WO | 2011/140446 | 11/2011 |
| WO | 2014/136494 | 9/2014 |
| WO | 2015/062640 | 5/2015 |
| WO | 2016/097170 | 6/2016 |
| WO | 2017/182347 | 10/2017 |
| WO | 2020/229192 | 11/2020 |
| WO | 2021/115649 | 6/2021 |
| WO | 2021/115650 | 6/2021 |

OTHER PUBLICATIONS

International Search Report dated Dec. 17, 2020, in PCT/EP2020/075961, 5 pages.
International Search Report dated Dec. 18, 2020, in PCT/EP2020/075962, 4 pages.
Liu et al., "A paradigm shift in enteric coating: Achieving rapid release in the proximal small intestine of man", Journal of Controlled Release, vol. 147, 2010, pp. 242-245.
Written Opinion dated Dec. 17, 2020, in PCT/EP2020/075961, 8 pages.
Written Opinion dated Dec. 18, 2020, in PCT/EP2020/075962, 6 pages.
U.S. Appl. No. 17/757,043, filed Jun. 8, 2022, 2023/0012981, Haksar et al.
U.S. Appl. No. 17/757,055, filed Jun. 8, 2022, 2023/0048354, Haksar et al.
U.S. Appl. No. 17/595,147, filed Nov. 10, 2021, 2022/0241155, Jain et al.
U.S. Appl. No. 12/742,263, filed May 11, 2010, 2010/0255092, Ravishankar et al.
U.S. Appl. No. 14/911,491, filed Feb. 11, 2016, 2016/0193182, Joshi et al.
U.S. Appl. No. 14/889,741, filed Nov. 6, 2015, 2016/0081933, Hensel et al.
NDA 20-406, Prevacid Lansoprazole Delayed-Release Capsules and Prevacid (lansoprazole) for Delayed-Release Oral Suspension, (Nos. 1541, 3046, 7309, 7311) TAP DN038-V2-Rev., TAP DN038-V1-Rev., 1995, 2002 TAP Pharmaceutical Products Inc., 34 pages.
Devarakonda et al., "Effect of pH on the solubility and release of furosemide from polyamidoamine (PAMAM) dendrimer complexes ", International Journal of Pharmaceutics, 2007, vol. 345, pp. 142-153.

* cited by examiner

DOSAGE FORM COMPRISING AN ALKALINE AGENT AND AN ENTERIC COATING LAYER

CROSS-REFERENCE TO RELATED APPLICATIONS

This application is the National Stage entry under § 371 of International Application No. PCT/EP2020/075960, filed on Sep. 17, 2020, and which claims the benefit of priority to Indian Application No. 201941051238, filed on Dec. 11, 2019. The content of each of these applications is hereby incorporated by reference in its entirety.

BACKGROUND OF THE INVENTION

Field of the Invention

The invention is in the field of pharmaceuticals and nutraceuticals, especially in the field of dosage forms comprising an alkaline agent in an intermediate coating layer and an enteric coating layer.

Background Description of Related Art

U.S. Pat. No. 4,786,505 describes an oral pharmaceutical preparation comprising (a) a core region comprising an effective amount of a material selected from the group of omeprazole plus an alkaline reacting compound, an alkaline omeprazole salt plus an alkaline compound and an alkaline omeprazole salt alone, (b) an inert subcoating which is soluble or rapidly disintegrating in water disposed on said core, said subcoating comprising one or more layers of materials selected from among tablet excipients and polymeric film-forming compounds; and (c) an outer layer disposed on said subcoating comprising an enteric coating. The subcoating layer also serves as a pH-buffering zone. The pH buffering properties of subcoating layer may be further strengthened by introducing substances chosen from a group of compounds usually used in antacid formulations such as, for instance, magnesium oxide, hydroxide or carbonate, aluminium or calcium hydroxide, carbonate or silicate; composite aluminium/magnesium compounds such as, for instance [$Al_2O_3 \cdot 6MgO \cdot CO_2 \cdot 12H_2O$ or $MgO \cdot AlO_3 \cdot 2SiO_2 \cdot n\text{-}H_2O$], wherein n is not an integer and less than 2. The object of U.S. Pat. No. 4,786,505 is to provide an enteric coated dosage form of omeprazole, which is resistant to dissolution in acid media and which dissolves rapidly in neutral to alkaline media and which has a good stability during long term storage. In examples 1 and 6 of U.S. Pat. No. 4,786,505 the percentage of alkaline substance (magnesium oxide or aluminium hydroxide/magnesium carbonate) in the subcoating layer, calculated on the weight of alkaline agent and the enteric polymer (hydroxypropyl methylcellulose phthalate) in the enteric coating layer is about 4.1 or 6.6% by weight respectively.

US2005/0214371A1 describes a stable composition of an acid labile drug, comprising a) an inner core with the acid labile drug; b) a first intermediate coating devoid of an alkaline stabilizing agent and the acid labile drug; c) a second intermediate coating comprising an alkaline stabilizing agent; and d) an outer enteric layer, wherein the acid labile drug can degrade at pH 3. The term "acid labile drug" refers to any drug or medicament or active pharmaceutical ingredient (API) that will degrade at a pH of 3. Examples of "acid labile drug" include pharmaceutically active substituted benzimidazole compounds, statins (e.g. pravastatin, fluvastatin and atorvastatin), antibiotics (e.g. penicillin G, ampicillin, streptomycin, clarithromycin and azithromycin), dideoxy cytosine (ddC), digoxin, pancreatin, bupropion and pharmaceutically acceptable salts thereof, such as buprion HCl. The term "pharmaceutically active substituted benzimidazole compound" refers to any pharmaceutically active substituted 2-(2-pyridylmethyl)-sulfinyl-1H-benzimidazole compound (e.g. lansoprazole, omeprazole, hydroxy omeprazole, pantoprazole, rabeprazole, esomeprazole, preprazole, pariprazole, rabeprazole and tenatoprazole) and pharmaceutically active substituted 2-(phenylmethy)-sulfinyl-1H-benzimidazole compound (e.g. leminoprazole). US2005/0214371A1 does not mention or suggest an unexpected release of the acid labile drugs at low pH values.

US2005/0214371A1 also provides a method of treating a disease selected from gastric or duodenal ulcer, severe erosive esophagitis, Zolinger-Elison syndrome, gastroesophageal reflux and *H. pylori* infection, comprising an effective amount of a stable pharmaceutical composition of the invention to a subject inflicted with the disease, preferably a subject in need of the treatment, wherein the acid labile drug in the stable pharmaceutical composition is selected from lansoprazole, omeprazole, pantoprazole, rabeprazole, hydroxy omeprazole, esomeprazole, pariprazole, preprazole, tenatoprazole, leminoprazole, and acceptable salts thereof.

IPCOM000009757D (IP.com Prior Art Database Technical Disclosure IP.com Number IPCOM000009757D, IP.com electronic publication date Sep. 17, 2002, Authors et al.: Disclosed Anonymously) describes "Stabilized Pharmaceutical Formulation of an Acid labile Benzimidazole Compound and its Preparation". The general disclosure IPCOM000009757D is very similar to that of US2005/0214371A1 with the exception that no "b) a first intermediate coating devoid of an alkaline stabilizing agent and the acid labile drug" is mentioned.

U.S. Pat. No. 7,932,258 B2 describes the use of a partially neutralized (meth)acrylate copolymer as a coating for the production of a medicament pharmaceutical form releasing active substance at reduced pH values.

WO 2008/135090A1 ("Duocoat Technology") describes dosage forms comprising two individual coatings that may comprise an inner coating comprising a partially neutralized anionic (meth)acrylate copolymer or a water soluble neutral polymer in combination with a C2-C16 carboxylic acid and an outer coating comprising an anionic (meth)acrylate copolymer, which is less neutralized than the material of the inner coating or not neutralized at all. The intended effect is that in vivo the solid dosage form releases its active substance "earlier", namely already at the entry of the intestine. The term "earlier" here means that the solid dosage form according to the invention starts to release the active substance already at lower pH value compared to the normal pH of the intestine, namely when the solid dosage form is transferred from the stomach to the entry of the intestine (e.g. pH 5.6) which is having a higher pH compared to the stomach, but not as high as it is the case in more distal sections of the intestine. In comparison to a standard EUDRAGIT® L100-55 coating, which shows almost no active ingredient release at pH 5.6, the double coating system releases around 30% of the active ingredient at the same pH in 45 min.

SUMMARY OF THE INVENTION

U.S. Pat. No. 4,786,505, US2005/0214371A1 and IPCOM000009757D provide stable pharmaceutical compositions for acid labile substances such as substituted benzimidazole compounds, especially the omeprazole or pantoprazole substance family. To provide pH stability during storage conditions a buffering alkaline substance is included in an intermediate coating layer. An outer enteric coating layer shall protect the substances from contact with the gastric acid. No data are available in U.S. Pat. No. 4,786,505, US2005/0214371A1 and IPCOM000009757D about the release of biologically active ingredients at pH values being present after the stomach passage. This may be reasoned by the teaching limited to the acid labile character of the chosen substances, for which it would not make too much sense to attempt a release at pH values already between 3 and 5.5.

WO 2008/135090A1 describes dosage forms comprising two individual coatings that may comprise an inner coating comprising a partially neutralized anionic (meth)acrylate copolymer or a water-soluble neutral polymer in combination with a C2-C16 carboxylic acid and an outer coating comprising an anionic (meth)acrylate copolymer, which is less neutralized than the material of the inner coating or not neutralized at all. The intended effect is that in vivo the solid dosage form releases its active substance faster namely already at the entry of the intestine. The effect seems to be limited to pH values not below around pH 5.6.

U.S. Pat. No. 7,932,258 B2 describes the use of a partially neutralized (meth)acrylate copolymer as a coating for the production of a medicament pharmaceutical form releasing active substance at reduced pH values. However, in practice, the reported effect of the single coating system seems to be alleviated when the compositions are tested first for 2 hours in acidic medium pH 1.2 and then at media with low pH between 3 and 5.

SUMMARY OF THE INVENTION

There is a need for dosages forms which are suitable to start the release of biologically active ingredients already at pH values directly after the stomach passage, i.e. at pH values about between 3 and 5.5. The objects of the invention are solved as described below.

Dosage Form

The invention is concerned with a dosage form comprising a) a core, comprising a biologically active ingredient, which is stable to a degree of at least 95% at pH 3 for 2 hours at 22° C., b) an intermediate coating layer (ICL) onto or above the core, comprising an alkaline agent and c) an enteric coating layer (ECL) onto or above the intermediate coating layer, comprising an enteric polymer, wherein the relation in percent of the alkaline agent in the ICL to the enteric polymer in the ECL is 5 to 95% calculated by the formula:

$$\frac{\text{quantity of alkaline agent in grams in the } ICL}{(\text{quantity of alkaline agent in grams in the } ICL + \text{quantity of enteric polymer in grams in the } ECL)} \times 100$$

The dosage form may usually have the form of the core, however coated with the intermediate coating layer and the enteric coating layer as disclosed, e.g. the form of a (coated) pellet (core). Furthermore, several single dosage forms may be contained in multiple as parts of a multi-unit dosage form, e.g. contained in a capsule or in a tablet in which a multiple of inventive dosage forms are contained, e.g. in the form of (coated) pellet (cores).

The dosage form may have the form of, for instance, a tablet, a minitablet, a pellet, a pill, a granule, a sachet or a capsule. The dosage form may as well be contained, preferably in multi-units, for instance, in a tablet, in a sachet or in a capsule.

DETAILED DESCRIPTION OF THE INVENTION

Release of the Biologically Active Ingredient

Preferably the release of the biologically active ingredient is 10% or less at pH 1.2 for 120 min and 50% or more (50-100%), preferably 60 to 100%, at a pH from 3 to 5.5, preferably at a pH from 3.2 to 5.0, for 45 min. The pH 1.2 test medium may be 0.1 N HCl according to USP, for instance USP 42, pH 3 to 5.5 media may be buffered media according to USP, for instance USP 42 (2019).

Core

The core of the dosage form comprises a biologically active ingredient.

The core of the dosage form may comprise the biologically active ingredient distributed in a matrix structure or bound in a binder in a coating on an inner core structure or enclosed in a capsule.

The core may be prepared by methods such as granulation, extrusion, spheronization or hot melt extrusion.

The core may be a pellet, a pill, a granule, a tablet or a capsule. The core may be an active ingredient-containing tablet, a pellet-containing compressed tablet, a mini-tablet or a capsule (hard or soft), which may be filled with active ingredient-containing pellets or granules, with a drug solution or dispersion, with mini-tablets or powder or combinations thereof.

The core may comprise for instance an uncoated pellet, a neutral carrier pellet, for instance a sugar sphere or nonpareilles, on top of which the biologically active ingredient is bound in a binder, such as lactose, polyvinyl pyrrolidone or a neutral cellulose-derivates such as HPC or HPMC. The binder-coating layer with the biologically active ingredient is considered herein as part of the core. The binder-coating layer of the core has, in contrast to the intermediate coating layer and the enteric coating layer, essentially no influence on the controlled release of the biologically active ingredient. The core may as well comprise an uncoated pellet consisting of a crystallized biologically active ingredient.

The core may comprise 0.1 to 100, 1 to 100, 2 to 90, 5 to 85, 10 to 70, 15 to 50% by weight of the biologically active ingredient. The core may comprise 0 to 99.9, 0 to 99, 10 to 98, 15 to 95, 30 to 90 or 50 to 85% by weight of pharmaceutical or nutraceutical acceptable excipients. The biologically active ingredient and the pharmaceutical or nutraceutical acceptable excipients may add up to 100

Biologically Active Ingredient

The dosage form comprises a core, comprising a biologically active ingredient which is stable to a degree of at least 95% in a test medium at pH 3 for 2 hours at 22° C. The "at least 95%" (95% or more) limit herein is derived from the United States Pharmacopeia, USP 42 (2 (2019)) Oral Drug Products—Product Quality Tests—"Universal Test for Oral Drug Products"—"Assay". " . . . . In general the a priori acceptance of +/−10% variation in limits of a quality attribute (e.g. assay) from the target label claim (100%) in most cases is intended to account lbr manufacturing variability and shelf-life stability and is primarily based on the notion that such variation in quality attribute is less likely to have a noticeable adverse impact on the desired clinical outcome. Acceptance criteria of 95.0%-105.0% are used with justification (e.g. for drug products with narrow therapeutic index), Activity assays and absolute content assays also are acceptable when justified.". Thus, a biologically active ingredient, which is stable to a degree of at least 95% in a test medium at pH 3 for 2 hours at 22° C. can be deemed to be to be a stable biologically active ingredient at pH 3 with no noticeable adverse impact on the desired (clinical) outcome. Such a biologically active ingredient can be further deemed to be stable to a degree of at least 95% for 2 hours at 22° C. at any pH in the pH range from 3.0 to 7.0. Stability in the pH range from 3.0 to 7.0 may be determined by a skilled person accordingly to the principles of the measurement of the stability at pH 3.0 as explained above, which means again (in buffered medium) for 2 hours at 22° C. at any pH in the pH range from 3.0 to 7.0.

The degree of stability of the biologically active ingredient may tested in an assays such as cited and described in USP 42 (2 (2019)) Oral Drug Products—Product Quality Tests, and there especially under—"Universal Test for Oral Drug Products"—"Identification" as possible chromatographic assay procedures, especially: Thin-Layer Chromatographic Identification tests (201) Spectrometric Identification Test (197), Nuclear Magnetic Resonance Spectroscopy (761), Near-Infrared Spectroscopy (1119) or Raman spectroscopy (1120) among others.

A test medium at pH 3 is a medium which is suitable for testing the stability respectively the degradation of the biologically active ingredient. The medium is usually an aqueous medium buffered at pH 3.0. The pH 3.0 medium assay may be for instance a buffered medium of 0.25 M disodium hydrogen phosphate anhydrous ($Na_2HPO_4$) aqueous solution adjusted to pH 3.0 with ortho-phosphoric acid. Stable to a degree of at least 95% of the biologically active ingredient from initially calculated 100% of biologically active ingredient are detectable after 2 hours incubation in the pH 3.0 medium. The degree of stability may be determined as discussed above by chromatographic or spectrometric methods as well known to a skilled person in the fields of biology, biochemistry, pharmacy and galenic and as described in pharmacopeias such as USP 42 (USP42 page information cited: USP42-NF37 1S-9007, USP42-NF37-6344, USP41-NF36-NF-5921, most recently appeared in Pharmacopeial Forum: Volume No. 44(2), 2019.

Thus, the biologically active ingredient is, in contrast to US2005/0214371A1, a "pH 3 acid-stable drug" which is stable, preferably stable to a degree of at least 95%, in a pH 3 medium for 2 hours at 22° C. Biologically active ingredients cover a wide chemical spectrum. Therefore, individual stability tests, media (buffers) and detection methods for individual biologically active ingredients should be based on the relevant pharmacopeia monographs in which the biologically active ingredient or active pharmaceutical ingredient (API) is listed. A skilled person in the field of pharmacy is guided well by these pharmacopeia monographs and can select suitable media, assays and/or detection method conditions. Relevant Pharmacopeias are the United States Pharmacopeia, the European Pharmacopeia, or Japanese Pharmacopeia but are not limited thereto. Relevant shall be the individually selected monograph or Pharmacopeia in its latest version at the date of this application.

In contrast to US2005/0214371A1, which describes a stable composition of an pH 3 acid labile drug, wherein the acid labile drug can degrade at pH 3, the present application refers to a dosage form comprising an "acid stable drug", especially to a biologically active ingredient which is which is stable, preferably stable to at least 95% (5% or less degradation), in a pH 3 medium for 2 hours at 22° C.

Thus, the definition of a biologically active ingredient, which is stable, preferably stable to at least 95% (5% or less degradation at pH 3.0 (in a pH 3 medium) for 2 hours at 22° C., excludes "acid labile drugs" as generally defined in US2005/0214371A1 and excludes the examples of "acid labile drugs" as literally mentioned US2005/0214371A1. Examples of the excluded "acid labile drugs" that are literally mentioned in US2005/0214371A1 comprise pharmaceutically active substituted benzimidazole compounds, statins (e.g. pravastatin, fluvastatin and atorvastatin) antibiotics (e.g. penicillin G, ampicillin, streptomycin, clarithromycin and azithromycin), dideoxy cytosine (ddC), digoxin, pancreatin, bupropion and pharmaceutically acceptable salts thereof, such as bupropion HCl. The term "pharmaceutically active substituted benzimidazole compound" refers to any pharmaceutically active substituted 2-(2-pyridylmethyl)-sulfinyl-1H-benzimidazole compound (e.g. lansoprazole, omeprazole, hydroxy omeprazole, pantoprazole, rabeprazole, esomeprazole, preprazole, pariprazole, rabeprazole and tenatoprazole) and pharmaceutically active substituted 2-(phenylmethy)-sulfinyl-1H-benzimidazole compound (e.g. leminoprazole).

Biologically active ingredients according to the present application may be for instance gastro-irritant drugs which absorb in the small intestine. Biologically active ingredients according to the present application may be for instance acetyl salicylic acid, benazepril, bisacodyl, budesonide, carvedilol, etopside, quinidine, ketoconazole or sotalol.

Further biologically active ingredients according to the present application may be biotechnology derived products or microbiologically derived products and may be selected from, for instance, enzymes, hormones, liquid or solid natural extracts, oligonucleotides, DNA, RNA, mRNA, siRNA, Protacs (proteolysis targeting chimera), peptide hormones, therapeutic bacteria, prebiotics, probiotics, peptides, proteins, urology drugs, omega-3-fatty acids, anthocyanidines e.g. from bilberries, blueberries or black currants as antioxidants, vitamins and vaccines.

Intermediate Coating Layer

The intermediate coating layer (ICL) is onto to or above the inner core and is comprising an alkaline agent. The intermediate coating layer may comprise 10 to 75, preferably 10 to 50% by weight of the alkaline agent. The intermediate layer may comprise 30 to 95, preferably 90 to 50% by weight of further pharmaceutically or nutraceutically acceptable excipients, such as, for example, a polymeric binder, for instance a neutral water-soluble cellulose such as hydroxypropylmethylcellulose (HPMC) or hydroxypropylcellulose (HPC) or polyvinyl pyrrolidone (PVP), or a plasticizer or a anti tacking agent or combination thereof. The polymeric binder may also be a neutral or an anionic (meth)acrylate copolymer. Preferably the intermediate layer is onto the core with no other coating layers in between. The intermediate coating layer may be present in an amount of 5 to 100, preferably 7.5 to 50% by weight calculated on the weight of the core.

Alkaline Agent

The alkaline agent may be an alkali or an earth alkali metal salt. The alkaline agent may be, for instance, selected from calcium oxide, calcium carbonate, magnesium carbonate, magnesium oxide, sodium carbonate, sodium bicarbonate and sodium hydroxide or any mixtures thereof. Preferred alkaline agents are magnesium oxide or magnesium carbonate. The relation of the alkaline agent in the intermediate coating layer (ICL) to the enteric polymer in the enteric coating layer (ECL) is 5 to 95, preferably 7 to 80 when calculated by the formula:

$$\frac{\text{quantity of alkaline agent in grams in the } ICL}{(\text{quantity of alkaline agent in grams in the } ICL + \text{quantity of enteric polymer in grams in the } ECL)} \times 100$$

Plasticizer

A Plasticizer may be defined in that they achieve through physical interaction with a polymer a reduction in the glass transition temperature and minimum film forming temperature to promote film formation, depending on the added amount. Suitable substances usually have a molecular weight of between 100 and 20,000 and comprise one or more hydrophilic group(s) in the molecule, e.g. hydroxy ester or amino groups.

The intermediate coating layer or the enteric coating layer may comprise a plasticizer, which may be selected from the groups of alkyl citrates, glycerol esters, alkyl phthalates, alkyl sebacates, sucrose esters, sorbitan esters and polyethylene glycols. The intermediate coating layer may comprise a plasticizer, preferably about 2 to 50, preferably 5 to 25% by weight, which may be selected for instance from triethyl citrate (TEC), acetyl triethyl citrate (ATEC), diethyl sebacate and dibutyl sebacate (DBS), glycerol, propylene glycol, polyethylene glycols 200 to 20,000 and castor oil. A preferred plasticizer for the intermediate coating layer may be glycerine or triethyl citrate. A preferred plasticizer for the enteric coating layer may be triethyl citrate.

Enteric Coating Layer

The enteric coating layer is onto to or above the intermediate coating layer is comprising an enteric polymer and optionally pharmaceutically or nutraceutically acceptable excipients. The enteric coating layer may comprise 10 to 100, preferably 20 to 80% by weight of the enteric polymer. The enteric coating layer may comprise 90 to 0, preferably 80 to 20% by weight of pharmaceutically or nutraceutically acceptable excipients, such as, for example, a plasticizer or a anti tacking agent. Preferably the enteric coating layer is onto the intermediate coating layer with no other coating layers in between. The enteric coating layer may be present in an amount of 5 to 50% by weight calculated on the weight of the core and the intermediate layer.

Enteric Polymer

The enteric polymer in the further coating layer onto or above the intermediate coating layer may be selected from anionic (meth)acrylate copolymers, anionic celluloses, anionic polysaccharides and polyvinyl acetate phthalates or any mixtures thereof. The enteric coating layer may be present in an amount of 10 to 50% by weight calculated on the weight of the core and the intermediate layer.

Anionic (Meth)Acrylate Copolymer(s)

The enteric coating layer may comprise a (meth)acrylate copolymer selected from copolymers comprising polymerized units of methacrylic acid and ethyl acrylate, of methacrylic acid and methyl methacrylate of ethyl acrylate and methyl methacrylate or of methacrylic acid, methyl acrylate and methyl methacrylate, from a mixture of a copolymer comprising polymerized units of methacrylic acid and ethyl acrylate with a copolymer comprising polymerized units of methyl methacrylate and ethyl acrylate and a mixture of a copolymer comprising polymerized units of methacrylic acid, methyl acrylate and methyl methacrylate with a copolymer comprising polymerized units of methyl methacrylate and ethyl acrylate or any mixtures thereof.

The coating layer may comprise a (meth)acrylate copolymer comprising polymerized units of 40 to 60% by weight of methacrylic acid and 60 to 40% by weight of ethyl acrylate (type EUDRAGIT® L 100-55). A suitable second polymer is EUDRAGIT® L 100-55 (Evonik Nutrition & Care GmbH, Darmstadt, Germany), which is a copolymer comprising polymerized units of 50% by weight of methacrylic acid and 50% by weight of ethyl acrylate. EUDRAGIT® L 30 D-55 is a 30% by weight aqueous dispersion of EUDRAGIT® L 100-55. The glass transition temperature $T_{gm}$ of EUDRAGIT® L 100-55 is about 110° C.

The coating layer may comprise a (meth)acrylate copolymer comprising polymerized units of 5 to 15% by weight of methacrylic acid, 60 to 70% by weight of methyl acrylate and 20 to 30% by weight of methyl methacrylate (type EUDRAGIT® FS). A suitable copolymer is EUDRAGIT® FS which is a copolymer polymerized from 25% by weight of methyl methacrylate, 65% by weight of methyl acrylate and 10% by weight of methacrylic acid. EUDRAGIT® FS 30 D is a dispersion comprising 30% by weight EUDRAGIT® FS. The glass transition temperature $T_{gm}$ of EUDRAGIT® FS is about 45° C.

The coating layer may comprise a (meth)acrylate copolymer comprising polymerized units of 40 to 60% by weight of methacrylic acid and 60 to 40% by weight of methyl methacrylate (type EUDRAGIT® L 100). EUDRAGIT® L 100 is a copolymer polymerized from 50% by weight of methyl methacrylate and 50% by weight of methacrylic acid. The glass transition temperature $T_{gm}$ of EUDRAGIT® L 100 is about or somewhat above 150° C.

The coating layer may comprise a (meth)acrylate copolymer comprising polymerized units of 20 to 40% by weight of methacrylic acid and 60 to 80% by weight of methyl methacrylate (type EUDRAGIT® s 100). EUDRAGIT® s 100 is a copolymer polymerized from 70% by weight methyl methacrylate and 30% by weight methacrylic acid. The glass transition temperature $T_{gm}$ of EUDRAGIT® S 100 is about or somewhat above 160° C.

The coating layer may also comprise an anionic (meth) acrylate copolymer in the form of a core-shell polymer from two (meth)acrylate copolymers. The coating layer may comprise a (meth)acrylate copolymer which is a core-shell polymer, comprising 50 to 90, preferably 70 to 80% by weight of a core, comprising polymerized units of 60 to 80, preferably 65 to 75% by weight of ethyl acrylate and 40 to 20, preferably 35 to 25% by weight of methyl methacrylate, and 50 to 10, preferably 30 to 20% by weight of a shell, comprising polymerized units of 40 to 60, preferably 45 to 55% by weight of ethyl acrylate and 60 to 40, preferably 55 to 45% by weight of methacrylic acid.

A suitable core-shell polymer is EUDRAGIT® FL 30 D-55 (Evonik Nutrition & Care GmbH, Darmstadt, Germany), which is a commercially available 30% by weight aqueous dispersion of a copolymer from a two-stage emulsion polymerization process, with a core of about 75% by weight, comprising polymerized units of about 70% by weight of ethyl acrylate and 30% by weight of methyl methacrylate, and a shell of about 25% by weight, comprising polymerized units of 50% by weight ethyl acrylate and 50% by weight methacrylic acid. The glass transition temperature $T_{gm}$ of the polymer of EUDRAGIT® FL 30D-55 is about 8° C.

Anionic Celluloses

Anionic celluloses (chemically modified celluloses) may be selected from carboxymethyl ethyl cellulose and its salts, cellulose acetate phthalate, cellulose acetate succinate, cellulose acetate trimellitate, hydroxypropyl methyl cellulose phthalate and hydroxypropyl methyl cellulose acetate succinate or any mixtures thereof.

Anionic Polysaccharides

Anionic polysaccharides (not based on cellulose) with enteric properties may be selected from polymers such as shellac, chitosan, alginic acid and salts of alginic acid, e.g. sodium, potassium or ammonium alginate.

Pharmaceutically or Nutraceutically Acceptable Excipients

The core, in the intermediate layer or in the enteric coating layer may optionally comprise pharmaceutically or nutraceutically acceptable excipients. Such pharmaceutically or nutraceutically acceptable excipients may be selected from the group of antioxidants, brighteners, binding agents, such as lactose, polyvinyl pyrrolidone or neutral water-soluble celluloses, flavoring agents, flow aids, glidants, penetration-promoting agents, pigments, plasticizers, further polymers, pore-forming agents and stabilizers or any combinations thereof.

Items

The invention may be characterized by the following items:

1. Dosage Form Comprising
   a) a core, comprising a biologically active ingredient which is stable to a degree of at least 95% at pH 3 for 2 hours at 22° C.,
   b) an intermediate coating layer (ICL) onto or above the core, comprising an alkaline agent and
   c) an enteric coating layer (ECL) onto or above the intermediate coating layer, comprising an enteric polymer, wherein the relation in percent of the alkaline agent in the ICL to the enteric polymer in the ECL is 5 to 95% when calculated by the formula:

$$\frac{\text{quantity of alkaline agent in grams in the } ICL}{100 \, (\text{quantity of alkaline agent in grams in the } ICL + \text{quantity of enteric polymer in grams in the } ECL)} \times$$

2. The dosage form, according to item 1, wherein the core comprises the biologically active ingredient distributed in a matrix structure or bound in a binder in a coating on a core.

3. Dosage form, according to item 1 or 2, wherein the biologically active ingredient is selected from acetyl salicylic acid, benazepril, bisacodyl, budesonide, carvediol, etopside, quinidine, ketoconazole or sotalol, enzymes, hormones, liquid or solid natural extracts, oligonucleotides, DNA, RNA, mRNA, siRNA, Protacs (proteolysis targeting chimera), peptide hormones, therapeutic bacteria, prebiotics, probiotics, peptides, proteins, urology drugs, omega-3-fatty acids and their salts, anthocyanines e.g. from bilberries, blueberries or black currants, vitamins and vaccines.

4. Dosage form, according to one or more of items 1 to 3, wherein the alkaline agent is an alkali or an earth alkali metal salt.

5. Dosage form, according to one or more of items 1 to 4, wherein the alkaline agent is selected from calcium oxide, calcium carbonate, magnesium carbonate, magnesium oxide, sodium carbonate, sodium bicarbonate and sodium hydroxide or any combinations thereof.

6. Dosage form, according to one or more of items 1 to 5, wherein the alkaline agent is magnesium oxide or magnesium carbonate.

7. Dosage form, according to one or more of items 1 to 6, wherein the intermediate coating layer further comprises a plasticizer or a polymeric binder or both.

8. Dosage form, according to one or more of items 1 to 7, wherein the enteric polymer in the second coating layer is selected from anionic (meth)acrylate copolymers, anionic celluloses, anionic polysaccharides and polyvinyl acetate phthalates or any mixtures thereof.

9. Dosage form, according to one or more of items 1 to 8, wherein the anionic (meth)acrylate copolymers are selected from copolymers comprising polymerized units of methacrylic acid and ethyl acrylate, of methacrylic acid and methyl methacrylate and of methacrylic acid, methyl acrylate and methyl methacrylate or any mixtures thereof.

10. Dosage form, according to one or more of items 1 to 9, wherein the anionic celluloses are selected from carboxymethyl ethyl cellulose and its salts, cellulose acetate phthalate, cellulose acetate succinate, cellulose acetate trimellitate, hydroxypropyl methyl cellulose phthalate and hydroxypropyl methyl cellulose acetate succinate or any mixtures thereof.

11. Dosage form according to one or more of items 1 to 10, wherein the release of the biologically active ingredient is 10% or less at pH 1.2 for 120 min and 50% or more at a pH from 3 to 5.5 for 45 min.

12. Dosage form according to one or more of items 1 to 11, wherein the biologically active ingredient is stable to a degree of at least 95% for 2 hours at 22° C. at any pH in the pH range from 3.0 to 7.0.

13. Dosage form according to one or more of items 1 to 12, wherein the degree of stability of the biologically active ingredient is tested in an assay which is a thin-layer chromatographic identification test, a spectrometric identification test, a nuclear magnetic resonance spectroscopy, a near-infrared spectroscopy or a Raman spectroscopy.

14. Dosage form according to one or more of items 1 to 13, wherein the biologically active ingredient is stable to a degree of at least 95% at pH 3.0 for 2 hours at 22° C. in a buffered medium of 0.25 M disodium hydrogen phosphate anhydrous ($Na_2HPO_4$) aqueous solution adjusted to pH 3.0 with ortho-phosphoric acid.

15. Dosage form according to one or more of items 1 to 14, wherein the relation in percent of the alkaline agent in the ICL to the enteric polymer in the ECL is 7 to 80%.

16. Dosage form according to one or more of the preceding items, wherein the release of the biologically active ingredient is 10% or less at pH 1.2 for 120 min and 60 to 100% within the pH from 3.2 to 5.0 for 45 min.

17. Dosage form according to one or more of the preceding items, wherein core comprises 0.1 to 100, 1 to 100, 2 to 90, 5 to 85, 10 to 70 or 15 to 50% by weight of the biologically active ingredient.

18. Dosage form according to one or more of the preceding items, wherein the core comprises 0 to 99.9, 0 to 99, 10 to 98, 15 to 95, 30 to 90 or 50 to 85% by weight of pharmaceutical or nutraceutical acceptable excipients.

19. Dosage form according to one or more of the preceding items, wherein the intermediate coating layer (ICL) is present in an amount of 5 to 100% by weight calculated on the weight of the core.

20. Dosage form according to one or more of the preceding items, wherein the intermediate coating layer (ICL) is present in an amount of 7.5 to 50% by weight calculated on the weight of the core.

21. Dosage form according to one or more of the preceding items, wherein the intermediate coating layer (ICL) comprises 5 to 75% by weight of the alkaline agent.

22. Dosage form according to one or more of the preceding items, wherein the intermediate coating layer (ICL) comprises 10 to 50% by weight of the alkaline agent.

23. Dosage form according to one or more of the preceding items, wherein the enteric coating layer (ECL) is present in an amount of 5 to 50% by weight calculated on the weight of the core and the intermediate layer.

24. Dosage form according to one or more of the preceding items, wherein the enteric coating layer (ECL) comprises 10 to 100% by weight of the enteric polymer.

25. Dosage form according to one or more of the preceding items, wherein the enteric coating layer (ECL) comprises 20 to 80% by weight of the enteric polymer.

26. Dosage form according to one or more of the preceding items, wherein the enteric polymer comprises a (meth) acrylate copolymer comprising polymerized units of 40 to 60% by weight of methacrylic acid and 60 to 40% by weight of ethyl acrylate.

27. Dosage form according to one or more of the preceding items, wherein the enteric polymer comprises a (meth) acrylate copolymer comprising polymerized units of 5 to 15% by weight of methacrylic acid, 60 to 70% by weight of methyl acrylate and 20 to 30% by weight of methyl methacrylate.

28. Dosage form according to one or more of the preceding items, wherein the enteric polymer comprises hydroxypropyl methyl cellulose phthalate.

EXAMPLES

A. Definition of Acid Stable & Acid Labile Drugs:
1. Study Design:
  Solution stability of acid stable and acid labile drugs were checked at various pH conditions at 22° C. and at temperature 40° C. for defining acid stable and acid labile drugs.
  Benazepril HCl was selected as model drug for the acid stable category and pantoprazole sodium was selected as model drug for the acid labile drug category. Percentage assay of drug after exposure to different pH conditions at 22° C. as well as 40° C. were estimated based on that percentage degradation was calculated and this data is used for defining acid stable and acid labile drugs.
2. Analytical Methodology:
  a. Benazepril HCl API Solution Stability Studies at Different pH and Temperature:
A) Methodology:
  I. Buffer preparations for stability study:
  a. 0.1 N HCl preparation: 8.5 mL of conc. HCl (37.5%) was diluted to 1000 mL with water.
  b. Other buffer solution preparation: 0.25 M Di-Sodium hydrogen phosphate anhydrous (Na$_2$HPO$_4$) solution (35.49 g/L) was prepared in appropriate quantity and pH was adjusted to pH 3.0, pH 4.0, pH 7.0 and pH 9.0 using ortho-phosphoric acid.
  II. Standard preparation (Solution A): Accurately weighed about 40 mg of Benazepril working standard was transferred into a 100 ml volumetric flask. About 50 ml of mobile phase was added and sonicated to dissolve. Volume was made up to the mark with mobile phase. 5 ml of this solution was diluted to 50 ml with mobile phase (40 ppm). This solution was used as standard for chromatographic analysis.
  III. Sample preparation
  a. Standard stock solution preparation (solution B): Accurately weighed about 40 mg of Benazepril working standard was transferred into a 100 mL volumetric flask. About 50 ml of methanol was added and sonicated to dissolve. Volume was made up to the mark with methanol. This stock solution was used further for dilutions with buffers under study.
  b. Sample solution preparations: 5 mL of Solution B was diluted to 50 mL with each of the above buffers under study (0.1 N HCl, Buffer pH 3.0, Buffer pH 4.0, Buffer pH 7.0, Buffer pH 9.0) in different volumetric flasks. After dilution of the solutions, each solution was divided into two different volumetric flasks; one kept at Room temperature and another kept at 40° C. (using magnetic stirrer, with stirring speed of 360 rpm, solution temperature maintained at 40° C.).
  c. Time intervals for study: Immediately after dilution with respective buffer, the solutions were analysed chromatographically as 0.0 hr interval sample. The subsequent aliquots were then removed at 2.0 h, 4.0 h, and 24.0 hours from both the conditions (RT and 40° C.) and analyzed chromatographically. Percent concentration was calculated to study stability of API at different pH and temperature.
B) Chromatographic Conditions
  Column: Agilent Zorbax Eclipse XDB C18 column, 150× 4.6 mm, 5 μm or equivalent
  Mobile Phase: Buffer MeOH (36:64)
  Wavelength: 240 nm
  Column Temp: 25° C.
  Injection Volume: 20 μL
  Flow rate: 1 mL/minute
  Preparation of Buffer for Mobile Phase:
  Accurately weighed 2.25 g of Tetra butyl ammonium bromide (AR grade) transferred in 500 mL water and dissolved. 0.55 mL of Glacial acetic acid (HPLC grade) added to it and volume was made up to 1000 mL with water. The buffer was filtered through 0.45 μm nylon membrane filter.
b. Pantoprazole Sodium Solution Stability Studies at Different pH and Temperature:
A) Methodology:
I. Solution Preparations for Stability Study:
  a. 0.1 N HCl preparation: 8.5 ml of conc. HCl (37.5%) was diluted to 1000 ml with water.
  b. Buffer pH 5.5—Accurately weighed about 1 g of potassium dihydrogen phosphate, 2 g of Dipotassium hydrogen phosphate and 8.5 g of sodium chloride was weighed and transferred to 1-liter beaker. To this, 500 mL water was added, salts were dissolved, and volume was made up to 1000 mL with water. The pH was adjusted to 5.5+0.05 using ortho-phosphoric acid.
  c. Buffer pH 4.5—Accurately weighed about 2.99 g of Sodium acetate trihydrate was transferred to 1-liter beaker. To this 500 mL water was added, salts were dissolved, and volume was made up to 1000 mL with water. The pH of the solution was adjusted to 4.5 (*0.05) using glacial acetic acid.
  d. Buffer pH 3.0—Accurately weighed about 8.98 gram of citric acid anhydrous and 2.13 gram of Tri-sodium citrate dihydrate were transferred to 1-liter beaker. To this 500 mL water was added, salts were dissolved, and volume was made up to 1000 mL with water. The pH of the solution was adjusted to 3.0 (*0.05) using dilute NaOH.
  e. 0.5 N Sodium hydroxide solution-2 g of sodium hydroxide was dissolved in 100 mL of water.
  f. 0.02 N Sodium hydroxide solution-4 mL of 0.5 N NaOH solution was diluted to 100 mL with water.

II. Standard preparation (Solution A)—Accurately weighed about 40 mg of Pantoprazole Sodium working standard was transferred into a 100 mL volumetric flask. About 60 ml 0.02N NaOH and 4 mL acetonitrile was added and sonicated to dissolve. Volume was made up to the mark with 0.02 N sodium hydroxide solution. 5 ml of this solution was diluted to 100 ml with 0.02 N sodium hydroxide solution (20 ppm). This solution was used as standard for chromatographic analysis.

III. Sample preparation a. Standard stock solution preparation (solution B): Accurately weighed about 40 mg of Pantoprazole Sodium working standard was transferred into a 100 ml volumetric flask. About 50 ml of methanol was added and sonicated to dissolve. Volume was made up to the mark with methanol. This stock solution was used further for dilutions with buffers understudy.

b. Sample solution preparations: 5 ml of Solution B was diluted to 100 mL with each of the above buffers under study (0.1 N HCl, Buffer pH 3.0, Buffer pH 4.5, Buffer pH 5.5) in different volumetric flasks. After dilution the solutions, each solution was divided into two different volumetric flasks; one kept at Room temperature and another kept at 40° C. (using magnetic stirrer, with stirring speed of 360 rpm, solution temperature maintained at 40° C.).

c. Time intervals for study: Immediately after dilution with each buffer, 1 mL of each solution was immediately diluted with 1 mL of 0.5 N sodium hydroxide solution and was analyzed chromatographically as 0.0 hr interval sample. and analyzed as 0.0 hr. sample solution. The subsequent aliquots of all buffer solutions were then removed at 0.25 h, 0.5 h, 1.0 h and 2.0 hours from both the conditions (RT and 40° C.), diluted two times immediately with 0.5 N sodium hydroxide and analyzed chromatographically. Percent concentration was calculated to study stability of API at different pH and temperature.

B) Chromatographic Conditions

Column: Agilent Zorbax XDB Eclipse C8 column, 150× 4.6 mm, 5 μm

Mobile Phase: Water-Acetonitrile:Triethylamine (60:40: 1) pH adjusted to 7.0 (+0.05) with ortho-phosphoric acid Wavelength: 290 nm Column Temp: 30° C.

Injection volume: 10 μL

Flow rate: 1.0 mL/minute

3. Study Outcomes:

TABLE 1

Percent assay of Benazepril HCl after exposure with different pH conditions and temperature:

% Assay of Benazepril HCl in different pH conditions and temperature

| Temp | Time in Hour | pH | | | | |
|---|---|---|---|---|---|---|
| | | 1.2 | 3 | 4 | 7 | 9 |
| 22° C. | Initial | 101 | 100 | 100 | 100 | 101 |
| 40° C. | 2 | 100 | 99 | 99 | 100 | 99 |
| | 4 | 100 | 99 | 99 | 100 | 99 |
| | 24 | 99 | 98 | 98 | 97 | 91 |

TABLE 2

Percent assay of Pantoprazole Sodium after exposure with different pH conditions and temperature: % Assay of Pantoprazole Sodium in different pH conditions and temperature

| Temp | Time in min | pH | | | |
|---|---|---|---|---|---|
| | | pH 1.2 | pH 3.0 | pH 4.5 | pH 5.5 |
| 22° C. | Initial | 88 | 81 | 98 | 98 |
| | 15 | 27 | 32 | 97 | 98 |
| | 30 | 13 | 20 | 96 | 92 |
| | 60 | 7 | 5 | 94 | 94 |
| | 120 | 5 | 1 | 89 | 88 |
| 40° C. | 15 | 17 | 3 | 92 | 97 |
| | 30 | 6 | 2 | 89 | 86 |
| | 60 | 4 | 2 | 79 | 77 |
| | 120 | 3 | 1 | 64 | 53 |

B. Core Preparation:

1.0 Composition of Core:

2.1 Composition of Benazepril & Sotalol Pellets:

TABLE 3

Composition of Benazepril & Sotalol pellets:

| | Formula for | | |
|---|---|---|---|
| | BENAZEPRIL PELLETS | SOTALOL PELLETS Experiment ID | Composition in grams * |
| | I1 to I10, C5 & C6 | I11 to I14 | I1 |
| Ingredients | Composition (% w/w) | | grams |
| NPS 20/25# (707-841 μm) | 64.78 | 70.92 | 259.09 |
| Benazepril | 20.11 | . . . | 80.43 |
| Sotalol | . . . | 21.28 | . . . |
| HPMC [3 cps] | 10.12 | 5.32 | 40.48 |
| Lactose | 2.50 | . . . | 10.00 |
| Aerosil 200 | 2.50 | 2.48 | 10.00 |
| Water (q.s. to % w/w solids) | q.s. to 25% | q.s. to 27% | q.s. to 25% |
| Total | 100 | 100 | 400 |

* Note:
Composition of Experiment I1 is also expressed in grams for demonstrating Percentage alkali on alkali and enteric polymer calculation. Quantities of ingredients in subsequent experiments can be calculated likewise.
Abbreviations:
NPS: Non-pareil seeds,
HPMC: Hydroxy propyl methyl cellulose;
cps: centipoise;
# refers to mesh 2.2 Composition of Sotalol Tablet:

TABLE 4

Composition of Sotalol tablet:

| Ingredients | Experiment ID I15 Composition (% w/w) |
|---|---|
| Intra-granular materials | |
| Sotalol Hydrochloride | 40.0 |
| Microcrystalline cellulose PH101 | 30.0 |
| Ac-Di-Sol ® (Croscarmellose sodium) | 2.5 |
| HPMC 3 cps | 1.5 |
| Water (q.s. to % w/w solids) | q.s.* |

TABLE 4-continued

| | |
|---|---|
| Composition of Sotalol tablet: | |

| Ingredients | Experiment ID<br>I15<br>Composition (% w/w) |
|---|---|
| Extra-granular materials | |
| Microcrystalline cellulose PH102 | 22.0 |
| Aerosil ® 200 Pharma | 1.0 |
| Croscarmellose sodium | 2.5 |
| Magnesium stearate | 0.5 |
| Total | 100 |
| Solid content of binder solution | 6.5% w/w |
| Water uptake | 30% w/w |

*q.s. to achieve granulation end point 2.0 Process for Core Preparation:

2.1 Process for Benazepril Pellets Preparation for Experiment I1 to I10, C5 & C6:

I. All the ingredients were weighed in required quantity.

II. HPMC [3 cps] was dissolved in water using overhead stirrer, till a clear solution is obtained.

III. Benazepril was sifted through 40 # (400 μm) sieve and mixed together with Lactose and Aerosil 200 in polybag for 2 min, then this blend was added to the solution of step II.

IV. Suspension was passed through 40# sieve and used for drug layering on NPS.

2.2 Process for Sotalol Pellets Preparation for Experiment I11 to I14:

I. All the ingredients were weighed in required quantity.

II. HPMC [3 cps] was dissolved in water using overhead stirrer, till a clear solution is obtained.

III. Sotalol was sifted through 40 # (400 μm) sieve and mixed together with Aerosil 200 in polybag for 2 min, then this blend was added to the solution of step II.

IV. Suspension was passed through 40# sieve and used for drug layering on NPS.

V. Used dehumidifier during spraying drug solution on NPS.

2.3 Process for Sotalol Tablets Preparation for Experiment I15:

I. Weigh all the ingredients as specified in the formula.

II. Sotalol hydrochloride, microcrystalline cellulose and Ac-Di-Solo were mixed uniformly and sifted through #30 mesh.

III. The powder blend of step II was added in to rapid mixture granulator and mixed for 3 min at slow speed.

IV. In a separate beaker, HPMC 3 cps was added slowly in purified water under continuous stirring to get a clear solution.

V. Step IV solution was then used to granulate dry mix of step III

VI. Granules were dried in tray dryer at 60° C. for 2 hr then passed through 30# sieve and then further dried for 4 hr at 60° C. till LOD was achieved below 5% w/w.

VII. Dried granules were passed through 30(595 μm) sieve.

VIII. Weighed all extra-granular materials accurately.

IX. Microcrystalline cellulose PH101, Ac-Di-Sol® and Aerosil 200 were mixed in polybag and then sifted through #A30 mesh.

X. Sotalol granules of step VII & sifted material of step IX were mixed in a double cone blender for 15 m at 15 RPM.

XI. Magnesium stearate (60 passed) was added to blend of step X and lubricated for 5 min at 15 RPM in double cone blender.

XII. Lubricated blend was used for tablet compression.

TABLE 5

| General Process Parameters for Benazepril<br>& Sotalol pellets (core) preparation: | | | |
|---|---|---|---|
| General Process Parameters<br>in GPCG 1.1, bottom spray | | I1 to I10,<br>C5 & C6 | I11 to I14 |
| Equipment setup | | | |
| Silicone tube inner diameter | mm | 3.0 | 3.0 |
| Air distribution plat | — | B | B |
| Column height | mm | 20 | 20 |
| Nozzle bore | mm | 0.8 | 0.8 |
| Process parameter setup | | | |
| Filter shaking mode | — | Asynchronous | Asynchronous |
| Filter shaking | sec | 5 | 5 |
| Filter shaking pause | sec | 100 | 100 |
| Air flow mode | — | Auto | Auto |
| Process data | | | |
| Air flow | CFM | 60-80 | 60-80 |
| Atomization pressure | bar | 1.2 | 1.2 |
| Inlet temperature | ° C. | 50-60 | 58-60 |
| Product temperature | ° C. | 40-44 | 40-44 |
| Spray rate | g/min | 3-13 | 2-10 |

TABLE 6

| General Process Parameters for Sotalol Tablet preparation: | | |
|---|---|---|
| General Process Parameters | | Experiment I15 |
| Granulation | | |
| Equipment | | Rapid mixer granulator |
| Process data | | |
| Dry mixing | Time | 15 minutes |
| | Impeller Speed | Slow |
| | Chopper Speed | . . . |
| Binder addition | Time | 5 minutes |
| | Impeller Speed | Slow |
| | Chopper Speed | . . . |
| Wet mixing | Time | 1 minute |
| | Impeller Speed | Slow |
| | Chopper Speed | Slow |
| Compression | | |
| Equipment | | Parle Elisabeth Tablet<br>compression machine<br>(ElizaPress-200) |
| Equipment setup | | |
| Shape of punch | | Circular, standard concave |
| Size of punch | | 8.0 mm |
| Upper punch | | Plain |
| Lower punch | | Plain |
| Process data | | |
| Weight of tablet | mg | 200.0 |
| Hardness | N | 60-90 |
| Thickness | Mm | 4.10-4.30 |
| Friability | % | 0.0-0.1 |
| Disintegration time | Minute | 2-4 |

C. Coating Composition:

1. Coating Composition for Intermediate and Enteric Coating on Benazepril Pellets:

TABLE 7(a)

| | Composition (% w/w) | | | | | Composition in gram* |
|---|---|---|---|---|---|---|
| Experiment No. | I1 | I2 | I3 | I4 | I5 | I1 |
| Core | BP | BP | BP | BP | BP | 326.53 |
| Intermediate coating step | | | | | | |
| HPMC [3 cps] | 44.44 | 44.44 | 44.44 | 44.44 | 66.67 | 32.65 |
| Glycerin | 11.11 | 11.11 | 11.11 | 11.11 | 16.67 | 8.16 |
| Magnesium oxide | 44.44 | . . . | . . . | . . . | 16.67 | 32.65 |
| Magnesium Carbonate | . . . | 44.44 | | | . . . | . . . |
| Calcium Oxide | . . . | . . . | 44.44 | . . . | . . . | . . . |
| Calcium Carbonate | . . . | . . . | . . . | 44.44 | . . . | . . . |
| Water (q.s to % w/w solid) | q.s. to 10% | q.s. to 10% | q.s. to 10% | q.s. to 10% | q.s. to 10% | q.s. to 10% |
| Total | 100 | 100 | 100 | 100 | 100 | 100 |
| % Polymer build up w.r.t. core pellets | 10% w/w | 10% w/w | 10% w/w | 10% w/w | 10% w/w | 10% w/w |
| Enteric coating step | | | | | | |
| EUDRAGIT L30D-55 | 62.5 | 62.5 | 62.5 | 62.5 | 62.5 | 80.00 |
| TEC | 6.25 | 6.25 | 6.25 | 6.25 | 6.25 | 8.00 |
| Talc | 31.25 | 31.25 | 31.25 | 31.25 | 31.25 | 40.00 |
| Water (q.s to % w/w solid) | q.s. to 20% | q.s. to 20% | q.s. to 20% | q.s. to 20% | q.s. to 20% | q.s. to 20% |
| Total | 100 | 100 | 100 | 100 | 100 | 528.00 |
| % Polymer build up w.r.t. intermediate coated pellets | 20% w/w | 20% w/w | 20% w/w | 14% w/w | 20% w/w | 20% w/w |

*Note:
Composition of Experiment I1 is also expressed in grams for demonstrating Percentage alkali on alkali and enteric polymer calculation. Quantities of ingredients in subsequent experiments can be calculated likewise.
Abbreviation:
BP: Benazepril pellets;
HPMC: Hydroxy Propyl Methyl Cellulose;
PVP: Polyvinyl Pyrrolidone;
TEC: Triethyl Citrate;
w.r.t.: with respect to TABLE 7(b)

Coating composition for Intermediate and enteric coating Experiment I6 to I10:

| Experiment No. | I6 | I7 | I8 | I9 | I10 |
|---|---|---|---|---|---|
| Core | BP | BP | BP | BP | BP |
| Intermediate coating step | | | | | |
| HPMC (3 cps) | 44.44 | 44.44 | . . . | . . . | 44.44 |
| PVP K-30 | . . . | . . . | 44.44 | . . . | . . . |
| EUDRAGIT L100 | . . . | . . . | . . . | 40.0 | . . . |
| Glycerin | 11.11 | 11.11 | 11.11 | 20.0 | . . . |
| TEC | . . . | . . . | . . . | . . . | 11.11 |
| Magnesium oxide | 44.44 | 44.44 | 44.44 | 40.0 | 44.44 |
| Liquid ammonia | . . . | . . . | . . . | q.s.* | . . . |
| Water (q.s to % w/w solid) | q.s. to 10% | q.s. to 10% | q.s. to 10% | q.s. to 10% | q.s. to 10% |
| Total | 100 | 100 | 100 | 100 | 100 |
| % Polymer build up w.r.t. core pellets | 10% w/w | 10% w/w | 10% w/w | 10% w/w | 10% w/w |
| Enteric coating step | | | | | |
| EUDRAGIT L30D-55 | . . . | . . . | 62.5 | 62.5 | 62.5 |
| EUDRAGIT FS30-D | 64.52 | . . . | . . . | . . . | . . . |
| HPMC HP-55 | . . . | 62.5 | . . . | . . . | . . . |
| TEC | 3.23 | 6.25 | 6.25 | 6.25 | 6.25 |
| Talc | 32.26 | 31.25 | 31.25 | 31.25 | 31.25 |
| Ethanol:Water :: 80:20 mixture | . . . | q.s. to 10% | . . . | . . . | . . . |

TABLE 7(b)-continued

| Coating composition for Intermediate and enteric coating Experiment I6 to I10: Composition (% w/w) | | | | | |
| --- | --- | --- | --- | --- | --- |
| Experiment No. | I6 | I7 | I8 | I9 | I10 |
| Water (q.s to % w/w solid) | q.s. to 20% | . . . | q.s. to 20% | q.s. to 20% | q.s. to 20% |
| Total | 100 | 100 | 100 | 100 | 100 |
| % Polymer build up w.r.t. intermediate coated pellets | 8% w/w | 18% w/w | 18% w/w | 15% w/w | 15% w/w |

*for Neutralisation to pH 7

Abbreviation:

BP: Benazepril drug layered pellets;

HPMC: Hydroxy Propyl Methyl Cellulose;

PVP: Polyvinyl Pyrrolidone;

TEC: Triethyl Citrate;

w.r.t.: with respect to

2. Composition and Process of Intermediate and Enteric Coating on Sotalol Pellets:

TABLE 8

| Coating composition for Intermediate and enteric coating of Experiment I11 to I15: Composition (% w/w) | | | | | |
| --- | --- | --- | --- | --- | --- |
| Experiment No. | I11 | I12 | I13 | I14 | I15 |
| Core | SP | SP | SP | SP | ST |
| Intermediate coating step | | | | | |
| HPMC (3 cps) | 44.44 | . . . | 66.67 | 50.0 | 40.0 |
| EUDRAGIT L100 | . . . | 40.0 | . . . | . . . | . . . |
| Glycerin | 11.11 | 20.0 | 16.67 | . . . | 20.0 |
| Magnesium oxide | 44.44 | 40.0 | 16.67 | 50.0 | 40.0 |
| Liquid ammonia | . . . | q.s.* | . . . | . . . | . . . |
| Purified water | q.s. to 10% | q.s. to 10% | q.s. to 10% | q.s. to 20% | q.s. to 10% |
| Total | 100 | 100 | 100 | 100 | 100 |
| % Polymer build up w.r.t. core pellets | 10% w/w | 10% w/w | 10% w/w | 30% w/w | 15 mg/cm$^2$ |
| Enteric coating step | | | | | |
| EUDRAGIT L30D-55 | 62.5 | 62.5 | 62.5 | 62.5 | 62.5 |
| TEC | 6.25 | 6.25 | 6.25 | 6.25 | 6.25 |
| Talc | 31.25 | 31.25 | 31.25 | 31.25 | 31.25 |
| Water (q.s to % w/w solid) | q.s. to 20% | q.s. to 20% | q.s. to 20% | q.s. to 20% | q.s. to 20% |
| Total | 100 | 100 | 100 | 100 | 100 |
| % Polymer build up w.r.t. intermediate coated pellets | 22% w/w | 18% w/w | 22% w/w | 25% w/w | 4 mg/cm$^2$ |

*for Neutralisation to pH 7

Abbreviations:

SP: Sotalol pellets;

ST: Sotalol Tablets;

HPMC: Hydroxy Propyl Methyl Cellulose;

TEC: Triethyl Citrate;

w.r.t.: with respect to

D. Coating Process:

1. Intermediate Coating:

1.1 Process for Experiment I1 to I8, I10, I11, I13 & I15 Intermediate Coating:

I. All the ingredients were weighed in required quantity.

II. Glycerol/TEC was dissolved in purified water.

III. HPMC (3 cps)/PVP K-30 was dissolved step II using overhead stirrer, till a clear solution is obtained.

IV. Magnesium oxide/Magnesium Carbonate/Calcium Oxide/Calcium Carbonate was added to above solution slowly while stirring and resulted suspension was allowed to mix for 30 min.

V. Suspension was passed through 40# sieve and used for intermediate coating on drug layered pellets.

1.2 Process for Experiment I9 & I12 Intermediate Coating:

I. All the ingredients were weighed in required quantity.

II. Disperse EUDRAGIT® L100 in $\frac{3}{4}^{th}$ quantity of water using overhead stirrer.

III. Adjust pH of step II to 7.0 using liquid ammonia.

IV. Add glycerol in step III and stir for 15 minutes using overhead stirrer.

V. Add Magnesium Oxide in step IV and stir for 15 minutes using overhead stirrer.

VI. Disperse talc in remaining quantity of water and homogenize for 20 minutes.

VII. Add step VI to step V and stir for 15 minutes.

VIII. Suspension was passed through 40# sieve and used for intermediate coating on drug layered pellets.

1.3 Process for Experiment I14 Intermediate Coating:

I. All the ingredients were weighed in required quantity.

II. HPMC (3 cps) was dissolved in water using overhead stirrer, till a clear solution is obtained.

III. Magnesium oxide was added to above solution slowly while stirring and resulted suspension was allowed to mix for 0 min.

IV. Suspension was passed through 40# sieve and used for intermediate coating on drug layered pellets.

2. Enteric Coating:

1.1 Process for Experiment I1 to I5, I8 to I15 Enteric Coating:

I. All the ingredients were weighed in required quantity.

II. TEC and Talc were homogenized in water for 15 min then added slowly to the EUDRAGIT® L 30 D-55 dispersion while stirring, resulted suspension was mixed for 30 min using overhead stirrer.

III. Suspension was passed through 40# sieve and used for enteric coating on intermediate coated pellets.

1.2 Process for Experiment I6 Enteric Coating:

I. All the ingredients were weighed in required quantity.

II. TEC and Talc were homogenized in water for 15 min then added slowly to the EUDRAGIT® FS30D disper-

TABLE 9

General Process Parameters for intermediate coating of inventive experiments:

| General Process Parameters in GPCG 1.1, bottom spray for intermediate coating | | Experiment I1 to I8, I10, I11, I13 & I14 | Experiment I9 & I12 | Experiment I14 |
|---|---|---|---|---|
| Equipment setup | | | | |
| Silicone tube inner diameter | mm | 3.0 | 3.0 | 3.0 |
| Air distribution plat | — | B | B | B |
| Column height | mm | 15-20 | 15 | 20 |
| Nozzle bore | mm | 0.8 | 0.8 | 0.8 |
| Process parameter setup | | | | |
| Filter shaking mode | — | Asynchronous | Asynchronous | Asynchronous |
| Filter shaking | sec | 5 | 5 | 3 |
| Filter shaking pause | sec | 250 | 100 | 180 |
| Air flow mode | — | Auto | Auto | Auto |
| Process data | | | | |
| Air flow | CFM | 75-90 | 90-99 | 97-151 |
| Atomization pressure | bar | 1.2 | 1.4 | 1.5 |
| Inlet temperature | ° C. | 55-58 | 45 | 50-55 |
| Product temperature | ° C. | 41-43 | 36-39 | 39-43 |
| Spray rate | g/min | 3-10 | 3-9 | 3-10 |

TABLE 10

General Process Parameters for intermediate coating of Experiment I15:

| General Process Parameters for intermediate coating | | Experiment I15 |
|---|---|---|
| Equipment used | | Neocota |
| Equipment setup | | |
| Silicone tube inner diameter | mm | 3.0 |
| Pan size | inch | 14 |
| Number of baffles | No. s | 6 |
| Process data | | |
| Pan RPM | RPM | 2-8 |
| Inlet temperature | ° C. | 70-73 |
| Product temperature | ° C. | 40-42 |
| Atomization pressure | bar | 1.5 |
| Spray rate | g/min | 3-5 | sion while stirring, resulted suspension was mixed for 30 min using overhead stirrer.

III. Suspension was passed through 40# sieve and used for enteric coating on intermediate coated pellets.

1.3 Process for Experiment I7 Enteric Coating:

I. All the ingredients were weighed in required quantity.

II. Dissolve HPMCP HP-55 in Ethanol-water mixture using overhead stirrer.

III. Add TEC and talc in step 2 and continue stirring for 15 minutes.

IV. Suspension was passed through 40# sieve and used for enteric coating on intermediate coated pellets.

TABLE 11

General Process Parameters for enteric coating of inventive experiments:

| General Process Parameters for enteric coating | | Experiment I1 to I5, I8 to I14 | Experiment I6 | Experiment I7 |
|---|---|---|---|---|
| Equipment used | | GPCG 1.1 bottom spray | Huttlin Mycrolab | Huttlin Mycrolab |
| *Equipment setup* | | | | |
| Silicone tube inner diameter | mm | 3.0 | 3.0 | 3.0 |
| Air distribution plate | — | B | NA | NA |
| Column height | m | 15-20 | NA | NA |
| Nozzle bore | mm | 0.8 | 0.8 | 0.8 |
| *Process parameter setup* | | | | |
| Filter operation | — | Auto | Manual | Manual |
| Filter shaking mode | — | Asynchronous | Asynchronous | Asynchronous |
| Filter shaking | sec | 5 | 0.2 | 0.2 |
| Filter shaking pause | sec | 250 | 1 | 1 |
| Air flow mode | — | Auto | Auto | Auto |
| *Process data* | | | | |
| Air flow | m³/hr | NA | 12 | 12 |
| | CFM | 70-80 | NA | NA |
| Atomization pressure | bar | 1.0 | 1.2 | 1.0 |
| Microclimate | bar | NA | 0.6 | 0.6 |
| Inlet temperature | ° C. | 38-41 | 31.6-32.3 | 32 |
| Product temperature | ° C. | 29-31 | 24-27.3 | 26.4-28.3 |
| Spray rate | g/min | 3-9 | 1-3 | 2-4 |

Abbreviation:
NA: Not applicable

TABLE 12

General Process Parameters for enteric coating of inventive Experiment I15:

| General Process Parameters for enteric coating | | Experiment I15 |
|---|---|---|
| Equipment used | | Neocota |
| *Equipment setup* | | |
| Silicone tube inner diameter | mm | 3.0 |
| Pan size | inch | 14 |
| Number of baffles | No. s | 6 |
| *Process data* | | |
| Pan RPM | RPM | 8-9 |
| Inlet temperature | ° C. | 45-50 |
| Product temperature | ° C. | 28-32 |
| Atomization pressure | bar | 1.2 |
| Spray rate | g/min | 3-4 |

E. Analysis of Enteric Coated Pellets:

Analytical Methodology

1. Benazepril Pellets:
A) Dissolution Conditions
1) Dissolution Parameters
   Apparatus: USP Type II
   Dissolution Medium: Acid stage medium for 2 hrs followed by buffer stage medium (1 hr)
   Volume of Medium: 750 mL for acid stage, 1000 mL for buffer stage
   Speed: 50 rpm
   Temperature: 37° C. t 0.5° C.
   Withdrawal Volume: 10 ml
2) Dissolution Mediums
   I. Acid stage medium—0.1 N HCl; Buffer stage medium—pH 5.5 buffer II. Acid stage medium—0.1 N HCl; Buffer stage medium—pH 4.5 buffer
   III. Acid stage medium—0.1 N HCl; Buffer stage medium—pH 3.0 buffer
3) Composition of Dissolution Mediums
   1) Buffer pH 5.5—
      1 g of Potassium dihydrogen phosphate, 2 g of Dipotassium hydrogen phosphate and 8.5 g of Sodium chloride was weighed and transferred to 1 liter beaker. To this, 500 mL water was added, salts were dissolved and volume was made up to 1000 mL with water. The pH was adjusted to 5.5 (t 0.05) using ortho-phosphoric acid
   2) Buffer pH 4.5—
      1 g of Potassium dihydrogen phosphate, 2 g of Dipotassium hydrogen phosphate and 8.5 g of Sodium chloride was weighed and transferred to 1 liter beaker. To this, 500 mL water was added, salts were dissolved, and volume was made up to 1000 mL with water. The pH was adjusted to 4.5 (t 0.05) using ortho-phosphoric acid
   3) Buffer pH 3.0—
      1 g of Potassium dihydrogen phosphate, 2 g of Dipotassium hydrogen phosphate and 8.5 g of Sodium chloride was weighed and transferred to 1-liter beaker. To this, 500 mL water was added, salts were dissolved, and volume was made up to 1000 mL with water. The pH was adjusted to 3.0 (t 0.05) using ortho-phosphoric acid
   4) Dissolution Procedure:
      Acid Stage: Accurately weighed pellets of Benazepril hydrochloride were transferred in different dissolution jars and then the dissolution test was performed as per parameters given in the method above (Acid Stage). After 2 hours 10 mL of aliquot was removed and analysed as acid stage sample solution.

Buffer Stage: The pellets after acid stage were transferred to buffer stage medium. The dissolution test was continued as per parameters given in the method above (Buffer Stage). The aliquots of each interval ware filtered through 0.45 μm nylon membrane syringe filter discarding first few mL of the filtrate and analysed as buffer stage sample solution.

B) Chromatographic Conditions

Column: Agilent Zorbax Eclipse XDB C18 column, 150× 4.6 mm, 5 μm or equivalent

Mobile Phase: Buffer:MeOH (36:64)

Wavelength: 240 nm

Column Temp: 25° C.

Injection Volume: 20 μL

Flow rate: 1 mL/minute

Preparation of Buffer for Mobile Phase:

Accurately weighed 2.25 g of Tetra butyl ammonium bromide transferred in 500 mL water and dissolved. 0.55 mL of Glacial acetic acid added to it and volume was made up to 1000 mL with water. The buffer was filtered through 0.45 μm nylon membrane filter.

2. Sotalol Pellets/Tablets:

A) Dissolution Conditions

1) Dissolution Parameters

Apparatus: USP Type II

Dissolution Medium: Acid stage medium for 2 hrs followed by buffer stage medium (1 hr)

Volume of Medium: 750 mL for acid stage, 1000 mL for buffer stage

Speed: 50 rpm

Temperature: 37° C. t 0.5° C.

Withdrawal Volume: 10 ml

2) Dissolution Mediums

IV. Acid stage medium—0.1 N HCl; Buffer stage medium—pH 5.5 buffer

V. Acid stage medium—0.1 N HCl; Buffer stage medium—pH 4.5 buffer

VI. Acid stage medium—0.1 N HCl; Buffer stage medium—pH 3.0 buffer

3) Composition of Dissolution Mediums

1) Buffer pH 5.5—

1 g of Potassium dihydrogen phosphate, 2 g of Dipotassium hydrogen phosphate and 8.5 g of Sodium chloride was weighed and transferred to 1 liter beaker. To this, 500 mL water was added, salts were dissolved and volume was made up to 1000 mL with water. The pH was adjusted to 5.5 (t 0.05) using ortho-phosphoric acid 2) Buffer pH 4.5—

1 g of Potassium dihydrogen phosphate, 2 g of Dipotassium hydrogen phosphate and 8.5 g of Sodium chloride was weighed and transferred to 1 liter beaker. To this, 500 mL water was added, salts were dissolved and volume was made up to 1000 mL with water. The pH was adjusted to 4.5 (t 0.05) using ortho-phosphoric acid 3) Buffer pH 3.0—

1 g of Potassium dihydrogen phosphate, 2 g of Dipotassium hydrogen phosphate and 8.5 g of Sodium chloride was weighed and transferred to 1 liter beaker. To this, 500 mL water was added, salts were dissolved and volume was made up to 1000 mL with water. The pH was adjusted to 3.0 (t 0.05) using ortho-phosphoric acid 4) Dissolution Procedure:

Acid Stage: Accurately weighed pellets or tablets of Sotalol were transferred in different dissolution jars and then the dissolution test was performed as per parameters given in the method above (Acid Stage). After 2 hours 10 mL of aliquot was removed and analyzed as acid stage sample solution.

Buffer Stage: The pellets or tablets after acid stage were transferred to buffer stage medium. The dissolution test was continued as per parameters given in the method above (Buffer Stage). The aliquots of each interval ware filtered through 0.45 μm nylon membrane syringe filter discarding first few mL of the filtrate and analyzed as buffer stage sample solution.

B) Chromatographic Conditions

Column: Agilent Zorbax Eclipse XDB C 18 column, 150×4.6 mm, 5 μm or equivalent

Mobile Phase: Buffer:ACN (90:10)

Wavelength: 238 nm

Column Temp: 25° C.

Injection Volume: 20 μL

Flow rate: 1.5 mL/minute

Preparation of Buffer for Mobile Phase:

Accurately weighed 6.8 g of potassium dihydrogen ortho-phosphate was dissolved in 1000 mL water. The buffer was filtered through 0.45 μm nylon membrane filter.

F. Summarization:

TABLE 13(a)

| | | | | |
|---|---|---|---|---|
| Performance of inventive experiments (Experiment I1 to I4): | | | | |
| Experiment No. | I1 | I2 | I3 | I4 |
| Objective | Experiment with different alkalis in inner layer | | | |
| Core | BP | BP | BP | BP |
| Inner layer (Intermediate coat) | 10% w/w coating of HPMC + Glycerol (25% )+ MgO (100%) | 10% w/w coating of HPMC 3 cps + Glycerol (25%) + MgCO3 (100%) | 10% w/w coating of HPMC 3cps + Glycerol (25%) + CaO (100%) | 10% w/w coating of HPMC 3cps + Glycerol (25%) + CaCO3 (100%) |
| Outer layer (Enteric coat) | 20% w/w coating of EUDRAGIT L30D-55 + TEC (10%) + Talc (50%) | 20% w/w coating of EUDRAGIT L30D-55 + TEC (10%) + Talc (50%) | 20% w/w coating of EUDRAGIT L30D-55 + TEC (10%) + Talc (50%) | 14% w/w coating of EUDRAGIT L30D-55 + TEC (10%) + Talc (50%) |

TABLE 13(a)-continued

| Performance of inventive experiments (Experiment I1 to I4): | | | | |
|---|---|---|---|---|
| Experiment No. | I1 | I2 | I3 | I4 |
| *Dissolution testing in acid media* | | | | |
| Enteric protection # | Pass | Pass | Pass | Pass |
| *Dissolution testing in buffer media of respective pH* | | | | |
| pH 5.5 * | 98.8 | 96.1 | 92.6 | 87.5 |
| pH 4.5 * | 101.3 | 98 | 87.5 | 0.6 |
| pH 4.0 * | 100.6 | . . . | . . . | . . . |
| pH 3.0 * | 86.4 | 76.3 | 11.8 | . . . |
| pH 2.0 * | 17.6 | 5.2 | . . . | . . . |
| % alkali in alkali + enteric polymer** | 28.98% w/w@ | 28.98% w/w | 28.98% w/w | 36.83% w/w |
| Inference | Enteric resistance followed by release in pH 3.0, 4.0, 4.5 & 5.5 is achieved using MgO as alkali. | Enteric resistance followed by release in pH 3.0, 4.5 & 5.5 is achieved using MgO as alkali. | Enteric protection followed by release in pH 5.5 & 4.5 is achieved using CaO as alkali. | Enteric protection followed by release in pH 5.5 alone is achieved using CaCO3 as alkali. |

Enteric protection after 2 hrs exposure to 0.1N HCl;

* Drug release after 45 mins;

**% alkali in alkali + enteric polymer =

$$\frac{\text{Quantity of alkaki (gm) in intermediate coat} \times 100}{\left[\begin{array}{l}\text{Qty. of alkali (gm) in intermediate coat} + \\ \text{Qty. of dry enteric polymer (gm) in enteric coat}\end{array}\right]}$$

@% alkali in alkali + enteric polymer for experiment I1

$$\frac{32.65}{[32.65 + 80.00]} \times 100 = 28.98\% \text{ w/w}$$

Abbreviation:

BP: Benazepril pellets; MgO : Magnesium Oxide; MgCO3: Magnesium Carbonate; CaO: Calcium oxide; CaCO3: Calcium carbonate; TEC: Triethyl Citrate; Qty: Quantity; gm: Grams TABLE 13(b)

| Performance of inventive experiments (Experiment I5 to I8): | | | | |
|---|---|---|---|---|
| Experiment No. | I5 | I6 | I7 | I8 |
| Objective | Experiment for use of trigger pH using varying level of alkali | Experiment with different enteric polymer in outer layer | | Experiment with different binder in inner layer |
| Core | BP | BP | BP | BP |
| Inner layer (Intermediate coat) | 10% w/w coating of HPMC + Glycerol (25%) + MgO (25%) | 10% w/w coating of HPMC 3cps + Glycerol (25%) + MgO (100%) | 10% w/w coating of HPMC 3cps + Glycerol (25%) + MgO (100%) | 10% w/w coating of PVP K 30 + Glycerol (25%) + MgO (100%) |
| Outer layer (Enteric coat) | 20% w/w coating of EUDRAGIT L30D-55 + TEC (10%) + Talc (50%) | 8% w/w coating of EUDRAGIT FS30-D + TEC (5%) + Talc (50%) | 18% w/w coating of HPMC HP-55 + TEC (10%) + Talc (50%) | 18% w/w coating of EUDRAGIT L30D-55 + TEC (10%) + Talc (50%) |
| *Dissolution testing in acid media* | | | | |
| Enteric protection # | Pass | Pass | Pass | Pass |
| *Dissolution testing in buffer media of respective pH* | | | | |
| pH 6.8 * | . . . | 94 | . . . | . . . |
| pH 5.5 * | 85.4 | 75 | . . . | 93.4 |
| pH 4.5 * | 57.1 | 59.9 | 81.9 | 93 |
| pH 4.0 * | . . . | . . . | . . . | |
| pH 3.0 * | 9.8 | . . . | 92.5 | 89.1 |
| % alkali in | 9.8% w/w | 50.5% w/w | 31.2% w/w | 31.2% w/w |

TABLE 13(b)-continued

| Experiment No. | I5 | I6 | I7 | I8 |
|---|---|---|---|---|
| alkali + enteric polymer** | | | | |
| Inference | Enteric resistance followed by release in pH 4.5 and 5.5 is achieved using 25% MgO (w.r.t. dry binder quantity in intermediate coat). Trigger pH release at desired pH is possible by varying alkali concentration in intermediate layer (Also use results of experiment C6 for comparison) | Enteric resistance followed by release in pH 6.8, 5.5 and 4.5 is achieved with EUDRAGIT FS 30-D as enteric polymer whose dissolution is beyond pH 7.2 | Enteric resistance followed by release in pH 3.0 & 4.5 is achieved with HPMC HP-55 as enteric polymer | Use of different binders in the intermediate coat is possible without affecting performance. |

Enteric protection after 2 hrs exposure to 0.1N HCl;
* Drug release after 45 mins;
**% alkali in alkali + enteric polymer =

Quantity of alkaki (gm) in intermediate coat × 100

$$\left[\begin{array}{l} \text{Qty. of alkali (gm) in intermediate coat +} \\ \text{Qty. of dry enteric polymer (gm) in enteric coat} \end{array}\right]$$

Abbreviation:
BP: Benazepril pellets; MgO: Magnesium Oxide; MgCO3: Magnesium Carbonate; CaO: Calcium oxide; CaCO3: Calcium carbonate; TEC: Triethyl Citrate; Qty.: Quantity; gm: Grams TABLE 13(c)

Performance of inventive experiments (Experiment I9 & I10):

| Experiment No. | I9 | I10 |
|---|---|---|
| Objective | Experiment with different binder in inner layer | Trial with different plasticizer in inner layer |
| Core | BP | BP |
| Inner layer (Intermediate coat) | 10% w/w coating of EUDRAGIT L 100 (Neutralized) + Glycerol (50%) + Magnesium oxide (100%) | 10% w/w coating of HPMC 3 cps + TEC (25%) + Magnesium oxide (100%) |
| Outer layer (Enteric coat) | 15% w/w coating of EUDRAGIT L30D-55 + TEC (10%) + Talc (50%) | 15% w/w coating of EUDRAGIT L30D-55 + TEC (10%) +Talc (50%) |
| | Dissolution testing in acid media | |
| Enteric protection # | Pass | Pass |
| | Dissolution testing in buffer media of respective pH | |
| pH 5.5 * | 101.5 | . . . |
| pH 4.5 * | . . . | . . . |
| pH 4.0 * | 97.4 | . . . |
| pH 3.0 * | 97.7 | 93.6 |
| % alkali in alkali + enteric polymer** | 34.78% w/w | 35.24% w/w |
| Inference | Use of different binders in the intermediate coat is possible without affecting performance. | Use of different plasticizers in the intermediate layer is possible without affecting performance. |

Enteric protection after 2 hrs exposure to 0.1N HCl;
* Drug release after 45 mins;
**% alkali in alkali + enteric polymer =

Quantity of alkaki (gm) in intermediate coat × 100

$$\left[\begin{array}{l} \text{Qty. of alkali (gm) in intermediate coat +} \\ \text{Qty. of dry enteric polymer (gm) in enteric coat} \end{array}\right]$$

Abbreviation:
BP: Benazepril pellets; MgO: Magnesium Oxide; MgCO3: Magnesium Carbonate; CaO: Calcium oxide; CaCO3: Calcium carbonate; TEC: Triethyl Citrate; Qty: Quantity; gm: Grams TABLE 13(d)

| Performance of inventive experiments (Experiment I11 to I14): | | | |
|---|---|---|---|
| Experiment No. | I11 | I12 | I13 | I14 |
| Objective | Experiment with different binder in intermediate layer on Sotalol pellets | | Experiment for use of trigger pH using lower level of alkali on Sotalol pellets | Experiment with higher percent alkali in alkali also without plasticizer in intermediate layer |
| Core | SP | SP | SP | SP |
| Inner layer (Intermediate coat) | 10% w/w coating of HPMC + Glycerol (25%) + MgO (100%) | 10% w/w coating of EUDRAGIT L 100 neutralized + Glycerol (50%) + MgO (100%) | 10% w/w coating of HPMC 3 cps + Glycerol (25%) + MgO (25%) | 30% w/w coating of HPMC 3 cps + Magnesium oxide (100%) |
| Outer layer (Enteric coat) EUDRAGIT L30D-55 + TEC (10%) + Talc (50%) | 22% w/w coating of EUDRAGIT L30D-55 + TEC (10%) + Talc (50%) | 18% w/w coating of EUDRAGIT EUDRAGIT L30D-55 + TEC (10%) + Talc (50%) | 22% w/w coating of EURAGIT L30D-55 + TEC (10%) + Talc (50%) | 25% w/w coating of |
| Dissolution testing in acid media | | | |
| Enteric protection # | Pass | Pass | Pass | |
| Dissolution testing in buffer media of respective pH | | | |
| pH 5.5 * | 96.9 | 93.15 | 83.4 | |
| pH 4.5 * | 95.3 | 73.98 | 87.5 | 84.0 |
| pH 4.0 * | . . . | . . . | . . . | . . . |
| pH 3.0 * | 89.7 | . . . | 5.6 | 54.7 |
| % alkali in alkali + enteric polymer** | 27.06% w/w | 30.77% w/w | 9% w/w | 42.9% w/w |
| Inference | Enteric resistance followed by release in pH 3.0, 4.5 & 5.5 is achieved using MgO as alkali. | Use of different binders in the intermediate coat is possible without affecting performance. | Enteric resistance followed by release in pH 4.5 and 5.5 is achieved using 25% MgO (w.r.t. dry binder quantity in intermediate coats). Trigger pH release at desired pH is possible by varying alkali concentration in intermediate layer | Higher percentage of alkali can be incorporated by increasing thickness of intermediate layer without affecting performance. Plasticizer in alkali (intermediate) layer does not have impact on performance of technology of invention |

\# Enteric protection after 2 hrs exposure to 0.1N HCl;

\* Drug release after 45 mins;

\*\*% alkali in alkali + enteric polymer =

$$\frac{\text{Quantity of alkaki (gm) in intermediate coat} \times 100}{\left[\begin{array}{l}\text{Qty. of alkali (gm) in intermediate coat} + \\ \text{Qty. of dry enteric polymer (gm) in enteric coat}\end{array}\right]}$$

Abbreviation:

SP: Sotalol pellets; MgO : Magnesium Oxide; MgCO3: Magnesium Carbonate; CaO: Calcium Oxide; CaCO3: Calcium Carbonate; TEC: Triethyl Citrate; Qty.: Quantity; gm: Grams

TABLE 13(e)

| Performance of Experiment I15: | |
|---|---|
| Experiment No. | I15 |
| Objective | Experiment with very high concentration of alkali in intermediate layer |
| Core | ST |
| Inner layer (Intermediate coat) | 15 mg/cm$^2$ coating of HPMC 3 cps + Glycerol (50%) + MgO (100%) |
| Outer layer (Enteric coat) | 4 mg/cm$^2$ coating of EUDRAGIT L30D-55 + TEC (10%) + Talc (50%) |
| Dissolution testing in acid media | |
| Enteric protection # | Pass |
| Dissolution testing in buffer media of respective pH | |
| pH 5.5 * | 98.7 |
| pH 4.5 * | 89.2 |
| pH 4.0 * | . . . |
| pH 3.0 * | 99.3 |
| % alkali in alkali + enteric polymer** | 77% w/w |
| Inference | Higher concentration of alkali can be used without affecting performance |

Enteric protection after 2 hrs exposure to 0.1N HCl;
* Drug release after 45 mins;
**% alkali in alkali + enteric polymer =

$$\frac{\text{Quantity of alkaki (gm) in intermediate coat} \times 100}{\left[\begin{array}{l}\text{Qty. of alkali (gm) in intermediate coat +}\\\text{Qty. of dry enteric polymer (gm) in enteric coat}\end{array}\right]}$$

Abbreviation:
ST: Sotalol Tablets; MgO: Magnesium Oxide; TEC: Triethyl Citrate; Qty.: Quantity; gm: Grams G. Core Preparation:
1. Composition of Benazepril, Sotalol and Pantoprazole Pellets (Core):

TABLE 14

Composition of Benazepril, Sotalol & Pantoprazole pellets (core) preparation for comparative experiments:

| | Formula for | | |
|---|---|---|---|
| | BENAZEPRIL PELLETS | SOTALOL PELLETS | PANTOPRAZOLE PELLETS |
| | | Experiment ID | |
| | C1-C3 | C4 | C7 |
| Ingredients | Composition (% w/w) | | |
| NPS 18/20# (850-1000 μm) | 64.05 | 68.90 | . . . |
| NPS 20/25# (707-841 μm) | . . . | . . . | 73.42 |
| Benazepril | 20.52 | . . . | . . . |
| Sotalol | . . . | 20.07 | . . . |
| Pantoprazole Sodium Sesquihydrate eq. to Pantoprazole 20% | . . . | . . . | 22.58 |
| HPMC [3 cps] | 10.33 | 10.03 | . . . |
| HPMC [6 cps] | . . . | . . . | 4.00 |
| Lactose | 2.55 | . . . | . . . |
| Aerosil 200 | 2.55 | 1.00 | . . . |
| Water (q.s. to % w/w solids) | q.s. to 20% | q.s. to 30% | q.s. to 20% |
| Total | 100 | 100 | 100 |

Abbreviations:
NPS: Non-pareil seeds,
HPMC: Hydroxy propyl methyl cellulose,
cps: centipoise 2. Process for Benazepril, Sotalol and Pantoprazole Pellets (Core):

2.1. Process for Benazepril Pellets Preparation for Experiment C1-C3:

I. All ingredients were weighed accurately.

II. Benazepril hydrochloride and lactose monohydrate were dissolved in sufficient quantity of purified water under continuous string.

III. In a separator beaker, HPMC 3 cps was dissolved in purified water under stirring.

IV. Aerosil® 200 was homogenized in purified water for 15 minutes.

V. Step II solution was added to step III under stirring.

VI. Step IV dispersion was then added to step V under stirring.

VII. Step VI suspension was then filtered through #60 mesh and use it for drug layering on NPS.

Process for Sotalol Pellets Preparation for Experiment C4:

I. Weighed all the ingredients as specified in the formula.

II. Sotalol hydrochloride was dissolved in sufficient quantity of purified water under continuous string.

III. In a separator beaker, HPMC 3 cps was dissolved in purified water under stirring.

IV. Aerosil® 200 was homogenized in purified water for 15 minutes.

V. Step II solution was added to step III under stirring.

VI. Step IV dispersion was then added to step V under stirring.

VII. Step VI suspension was then filtered through #60 mesh and use it for drug layering on NPS.

Process for Pantoprazole Pellets Preparation for Experiment C7:

I. All the ingredients were weighed in required quantity.

II. HPMC [6 cps] was dissolved in water using overhead stirrer, until a clear solution is obtained.

III. Pantoprazole Sodium Sesquihydrate was sifted through 40 # (400 μm) sieve and added to solution of step II during continuous stirring. Continued stirring till clear solution is obtained.

IV. Drug solution of step III was sifted through 40 # sieve and used for drug layering on NPS 20/25#.

TABLE 15

General Process Parameters for Benazepril, Sotalol and Pantoprazole pellets (core) preparation of comparative experiments:

| General Process Parameters in GPCG 1.1, bottom spray | | C1-C3 | C4 | C7 |
|---|---|---|---|---|
| Equipment setup | | | | |
| Silicone tube inner diameter | mm | 3.0 | 3.0 | 3.0 |
| Air distribution plat | — | B | B | C |
| Column height | mm | 20 | 20 | 20 |
| Nozzle bore | mm | 0.8 | 0.8 | 0.8 |
| Process parameter setup | | | | |
| Filter shaking mode | — | Asynchronous | Asynchronous | Asynchronous |
| Filter shaking | sec | 5 | 5 | 5 |
| Filter shaking pause | sec | 100 | 250 | 50 |
| Air flow mode | — | Auto | Auto | Auto |
| Process data | | | | |
| Air flow | CFM | 50-75 | 40-85 | 30-90 |
| Atomization pressure | bar | 1.0-1.1 | 1.0-1.1 | 1.0-1.4 |
| Inlet temperature | ° C. | 25-35 | 45-56 | 45-50 |
| Product temperature | ° C. | 20-25 | 20-25 | 32-38 |
| Spray rate | g/min | 2-8 | 2-6 | 3-8 |

H. Coating:

1.0 Coating Composition of Intermediate and Enteric Coating for Experiment C1 to C6:

TABLE 16(a)

Coating composition of Intermediate and enteric coating for experiments C1 to C6:

| | | Composition (% w/w) | | | | | |
|---|---|---|---|---|---|---|---|
| Experiment No. | | C1 | C2 | C3 | C4 | C5 | C6 |
| Core | | BP | BP | BP | SP | BP | BP |
| Intermediate coating step | | | | | | | |
| HPMC 3 cps | NA | | . . . | . . . | . . . | | 74.07 |
| EUDRAGIT L 100 | | | . . . | . . . | 57.14 | | . . . |
| EUDRAGIT L30D-55 | | | 56.50 | 56.50 | . . . | | . . . |
| Glycerin | | | . . . | . . . | 14.29 | | 18.52 |
| TEC | | | 2.82 | 2.82 | . . . | | . . . |
| Tween 80 | | | 1.13 | 1.13 | . . . | | . . . |
| Talc | | | 28.25 | 28.25 | 28.57 | | . . . |
| Magnesium Oxide | | | . . . | . . . | . . . | | 7.41 |
| Citric acid | | | 11.30 | 11.30 | . . . | | . . . |
| Sodium Hydroxide | | | q.s.*@ | q.s.*@ | . . . | | . . . |
| Liquid ammonia | | | . . . | . . . | q.s.** | | . . . |
| Water (q.s to % w/w solid) | | | q.s.to 10% | q.s.to 10% | q.s.to 10% | | q.s.to 10% |
| Total | | | 100 | 100 | 100 | | 100 |
| % Polymer build up | | | 8.5% | 8.5% | 10% | | 10% |

TABLE 16(a)-continued

Coating composition of Intermediate and enteric coating for experiments C1 to C6:

| | Composition (% w/w) | | | | | |
|---|---|---|---|---|---|---|
| Experiment No. | C1 | C2 | C3 | C4 | C5 | C6 |
| Core | BP | BP | BP | SP | BP | BP |
| w.r.t. core pellets | | | w/w | w/w | w/w | w/w |
| Enteric coating step | | | | | | |
| EUDRAGIT L30D-55 | 62.5 | 62.5 | 62.5 | 62.5 | 62.5 | 62.5 |
| TEC | 6.25 | 6.25 | 6.25 | 6.25 | 6.25 | 6.25 |
| Talc | 31.25 | 31.25 | 31.25 | 31.25 | 31.25 | 31.25 |
| Sodium Hydroxide | . . . | q.s. #@ | . . . | . . . | . . . | . . . |
| Water (q.s to %w/w solid) | q.s. to 20% | q.s. to 20% | q.s. to 10% | q.s. to 10% | q.s. to 20% | q.s. to 20% |
| Total | 100 | 100 | 100 | 100 | 100 | 100 |
| % Polymer build up w.r.t. intermediate coated pellets | 7 | 15 | 10 | 10 | 15 | 20 |

*for Neutralization to pH 6.0

**for Neutralization to pH 7; # for 30% Neutralization;

@ Used in the form of 1N NaOH solution; w.r.t.: with respect to

Abbreviations:

BP: Benazepril Pellets;

SP: Sotalol Pellets;

w.r.t.: with respect to

TABLE 16(b)

| Coating composition of Seal, Intermediate and enteric coating of comparative experiments C7: Composition (% w/w) | |
| --- | --- |
| Experiment No. | C7 |
| Core | PP |
| *Seal coating* | |
| HPMC (6 cps) | 40.61 |
| Talc | 59.39 |
| Water (q.s to | q.s. to |
| % w/w solid) | 15% |
| | |
| Total | 100 |
| % Polymer build up w.r.t. core pellets | 1.7% w/w |
| *Intermediate coating* | |
| Pharmacoat 606 | 40.0 |
| Magnesium Carbonate | 60.0 |
| Water (q.s to | q.s. to |
| % w/w solid) | 10% |
| | |
| Total | 100 |
| % Polymer build up w.r.t. seal coated pellets | 3.16% w/w |
| *Enteric coating* | |
| EUDRAGIT L30D-55 | 64.0 |
| TEC | 6.08 |
| Talc | 26.88 |
| Titanium Dioxide | 3.04 |
| Water (q.s to | q.s. to |
| % w/w solid) | 20% |
| | |
| Total | 100 |
| % Polymer build up w.r.t. intermediate coated pellets | 20% w/w |

Abbreviations:
PP: Pantoprazole Pellets;
w.r.t.: with respect to 2.0 Seal Coating:

2.1 Process of Seal Coating of Experiment C7:

I. All the ingredients were weighed in required quantity.

II. HPMC [6 cps] was dissolved in water using overhead stirrer, till a clear solution is obtained.

III. Talc was added to step II solution slowly while stirring and resulted suspension was allowed to mix for 30 min.

IV. Suspension was passed through 40# sieve and used for seal coating.

TABLE 17

| General Process Parameters for seal coating of comparative experiment C7: | | |
| --- | --- | --- |
| General Process Parameters in GPCG 1.1, bottom spray for seal coating | | Experiment C7 |
| *Equipment setup* | | |
| Silicone tube inner diameter | mm | 3.0 |
| Air distribution plate | — | C |
| Column height | mm | 15 |
| Nozzle bore | mm | 0.8 |
| *Process parameter setup* | | |
| Filter shaking mode | — | Asynchronous |
| Filter shaking | sec | 5 |
| Filter shaking pause | sec | 250 |
| Air flow mode | — | Auto |
| *Process data* | | |
| Air flow | CFM | 50-70 |
| Atomization pressure | bar | 1.0-1.4 |

TABLE 17-continued

| General Process Parameters for seal coating of comparative experiment C7: | | |
| --- | --- | --- |
| General Process Parameters in GPCG 1.1, bottom spray for seal coating | | Experiment C7 |
| Inlet temperature | ° C. | 45-50 |
| Product temperature | ° C. | 33-37 |
| Spray rate | g/min | 3-8 |

3.0 Intermediate Coating:

3.1 Process for Experiment C3 & C4 Intermediate Coating:

I. Weighed all ingredients as specified in the formula.

II. Weighed quantity of talc was dispersed in purified water under homogenizer for 30 min.

III. Separately prepared citric acid solution was added in step II.

IV. 1N NaOH solution required for neutralization of EUDRAGIT® L30D-55 was prepared.

V. In a separate glass beaker, TEC and Tween 80 were added in warmed purified water till to forms a clear solution.

VI. The step V solution was then added to the step II dispersion under overhead stirrer for 10 to 15 min.

VII. The required quantity EUDRAGIT® L30D-55 was added to step II dispersion and mixed.

VIII. The step VII dispersion was neutralized to pH 6.0 with step IV 1N sodium hydroxide solution under continuous stirring to form a clear dispersion.

IX. Suspension of step VIII was passed through 40# sieve and used for intermediate coating on drug layered pellets.

3.2 Process for Experiment C5 Intermediate Coating:

I. All the ingredients were weighed in required quantity.

II. Disperse EUDRAGIT® L100 in ¾$^{th}$ quantity of water using overhead stirrer.

III. Adjust pH of step II to 7.0 using liquid ammonia.

IV. Add glycerol in step III and stir for 15 minutes using overhead stirrer.

V. Disperse talc in remaining quantity of water and homogenize for 20 minutes.

VI. Add step V to step IV and stir for 15 minutes.

VII. Suspension was passed through 40# sieve and used for intermediate coating on drug layered pellets.

3.3 Process for Experiment C6 Intermediate Coating: Refer Intermediate Coating Process of Experiment I1.

3.4 Process for Experiment C7 Intermediate Coating:

I. All the ingredients were weighed in required quantity.

II. Pharmacoat 606 was dissolved in purified water using overhead stirrer.

III. Magnesium Carbonate was added to above solution slowly while stirring and resulted suspension was then allowed to mix for 30 min.

IV. Suspension was passed through 40# sieve and used for intermediate coating.

TABLE 18

General Process Parameters for Intermediate coating (Experiment: C3-C5 & C7)

| General Process Parameters in GPCG 1.1, bottom spray | | Experiment C3 & C4 | Experiment C5 | Experiment C7 |
|---|---|---|---|---|
| Equipment setup | | | | |
| Silicone tube inner diameter | mm | 3.0 | 3.0 | 3.0 |
| Air distribution plat | — | B | B | C |
| Column height | mm | 20 | 15 | 20 |
| Nozzle bore | mm | 0.8 | 0.8 | 0.8 |
| Process parameter setup | | | | |
| Filter shaking mode | — | Asynchronous | Asynchronous | Asynchronous |
| Filter shaking | sec | 5 | 5 | 5 |
| Filter shaking pause | sec | 100 | 100 | 250 |
| Air flow mode | — | Auto | Auto | Auto |
| Process data | | | | |
| Air flow | CFM | 50-75 | 90-99 | 50-70 |
| Atomization pressure | bar | 1.0-1.1 | 1.4 | 1.0-1.4 |
| Inlet temperature | ° C. | 25-35 | 45 | 41-45 |
| Product temperature | ° C. | 20-25 | 36-39 | 33-37 |
| Spray rate | g/min | 2-8 | 3-9 | 3-8 |

4.0 Enteric Coating:

4.1 Process for Experiment C1, C3 to C6 Enteric Coating: Refer Enteric Coating Process of Experiment I1

4.2 Process for Experiment C2 Enteric Coating:

I. All the ingredients were weighed in required quantity.

II. Add EUDRAGIT® L30D-55 in 60% quantity of water under stirring.

III. Prepare 1N sodium hydroxide solution using part of remaining quantity of water.

IV. Add step III to step II slowly under stirring.

V. Add TEC & talc in remaining quantity of water and homogenize it for 30 minutes VI. Add step V to step IV under stirring and continue stirring for 20 minutes.

VII. Suspension was passed through 40# sieve and used for enteric coating on intermediate coated pellets.

4.3 Process of Enteric Coating of Experiment C7:

I. All the ingredients were weighed in required quantity.

II. TEC and Talc were homogenized in water for 15 min then added slowly to the EUDRAGIT® L 30 D-55 dispersion while stirring, resulted suspension was mixed for 30 min using overhead stirrer.

III. Suspension was passed through 40# sieve and used for enteric coating.

TABLE 19

General Process Parameters for enteric coating of comparative experiments:

| General Process Parameters in GPCG 1.1, bottom spray | | Experiment C2 | Experiment C7 |
|---|---|---|---|
| Equipment setup | | | |
| Silicone tube inner diameter | mm | 3.0 | 3.0 |
| Air distribution plat | — | B | B |
| Column height | mm | 15 | 15 |
| Nozzle bore | mm | 0.8 | 0.8 |
| Process parameter setup | | | |
| Filter shaking mode | — | Asynchronous | Asynchronous |
| Filter shaking | sec | 5 | 5 |
| Filter shaking pause | sec | 100 | 250 |
| Air flow mode | — | Auto | Auto |

TABLE 19-continued

General Process Parameters for enteric coating of comparative experiments:

| General Process Parameters in GPCG 1.1, bottom spray | | Experiment C2 | Experiment C7 |
|---|---|---|---|
| Process data | | | |
| Air flow | CFM | 63-76 | 40-70 |
| Atomization pressure | bar | 1.5 | 1.0-1.4 |
| Inlet temperature | ° C. | 52-55 | 35-39 |
| Product temperature | ° C. | 39-44 | 29-32 |
| Spray rate | g/min | 1-7 | 3-8 |

I. Analysis of Enteric Coated Pellets:

Analytical Methodology

1. Benazepril Pellets: Refer Step C(1) for Analytical Methodology of Benazepril Pellets for Experiment C1 to C3, C5 & C6

2. Sotalol Pellets: Refer Step C(2) for Analytical Methodology of Sotalol Pellets for Experiment C4

3. Analytical Methodology of Pantoprazole Pellets for Experiment C7:

A) Dissolution Conditions

1) Dissolution Parameters

Apparatus: USP Type II

Dissolution Medium: Acid stage medium for 2 hrs. followed by buffer stage medium (1 hr)

Volume of Medium: 1000 mL for acid stage, 1000 mL for buffer stage

Speed: 50 rpm

Temperature: 37° C. t 0.5° C.

Withdrawal Volume: 10 ml

Sample Dilution: Dilute 10 mL of Aliquot with 2 mL of 0.5 N Sodium Hydroxide Solution immediately.

2) Dissolution Mediums

I. Acid stage medium—0.1 N HCl; Buffer stage medium—pH 5.5 buffer

II. Acid stage medium—0.1 N HCl; Buffer stage medium—pH 4.5 buffer

3) Composition of Dissolution Mediums

1) Buffer pH 5.5—

1 g of Potassium dihydrogen phosphate, 2 g of Di-potassium hydrogen phosphate and 8.5 g of Sodium chloride was weighed and transferred to 1-liter beaker. To this, 500 mL water was added, salts were dissolved, and volume was made up to 1000 mL with water. The pH was adjusted to 5.5 (t 0.05) using ortho-phosphoric acid.

2) Buffer pH 4.5—

Accurately weigh and transfer 2.99 g of Sodium acetate trihydrate to 1-liter beaker. To this add water to dissolve and make up volume to 1000 mL. Adjust the pH to 4.5 (*0.05) using glacial acetic acid.

3) Buffer pH 3.0—

Accurately weigh and transfer 8.98 gram of citric acid anhydrous and 2.13 gram of Tri-sodium citrate dihydrate in 1000 ml of water. Sonicate to dissolve. Adjust it to pH 3.5 (*0.05) using dilute NaOH.

4) Dissolution Procedure:

Acid Stage: Accurately weighed pellets of Pantoprazole were transferred in different dissolution jars and then the dissolution test was performed as per parameters given in the method above (Acid Stage). After 2 hours 10 mL of aliquot was removed, filtered through 0.45

µm PVDF membrane syringe filter. 1 mL was immediately diluted with 1 mL of 0.5 N sodium hydroxide solution and analyzed as acid stage sample solution.

Buffer Stage: The pellets after acid stage were transferred to buffer stage medium. The dissolution test was continued as per parameters given in the method above (Buffer Stage). The aliquots of each interval ware filtered through 0.45 µm PVDF membrane syringe filter discarding first few mL of the filtrate. 1 mL was immediately diluted with 1 mL of 0.5 N sodium hydroxide solution and analyzed as buffer stage sample solution.

B) Chromatographic Conditions

Chromatographic Conditions

Column: Agilent Zorbax XDB Eclipse C8 column, 150× 4.6 mm, 5 µm

Mobile Phase: Water-Acetonitrile:Triethylamine (60:40: 1) pH adjusted to 7.0 (+0.05) with orthophosphoric acid Wavelength: 290 nm Column Temp: 30° C.

Injection volume: 10 µL

Flow rate: 1.0 mL/minute

Summarization:

TABLE 20(a)

| Performance of comparative experiments C1 to C4: | | | | |
|---|---|---|---|---|
| Experiment No. | C1 | C2 | C3 | C4 |
| Objective | Standard EUDRAGIT L30D-55 coating | 30% Neutralized EUDRAGIT L30D-55 coating (according to US7932258B2) | "Duocoat Technology" (according to WO 2008/135090A1) | |
| Core | BP | BP | BP | BP |
| Inner layer (Intermediate coat) | . . . | . . . | 8.5% w/w EUDRAGIT L 30D55 neutralized at pH 6.0 with 20% citric acid + TEC (5%) + Talc (50%) | 8.5% w/w EUDRAGIT L30D-55 Neutralized at pH6.0 with 20% Citric acid + TEC (5%) + Talc (50%) |
| Outer layer (Enteric coat) | 7% w/w EUDRAGIT L30D-55 + TEC (10%) + Talc (50%) | 15% w/w EUDRAGIT L 30D55 (30% neutralized) with NaOH) + TEC (10%) +Talc (50%) | 10% w/w EUDRAGIT L30D-55 + TEC (10%) + Talc (50%) | 10% w/w EUDRAGIT L30D-55 + TEC (10%) +Talc (50%) |
| Dissolution testing in acid media | | | | |
| Enteric protection # | Pass | Pass | Pass | Pass |
| Dissolution testing in buffer media of respective | | | | |
| pH 6.2 | . . . | . . . | 72.6 * | 97.0@ |
| pH 5.8 | . . . | . . . | 6.2 * | 91.8@ |
| pH 5.5 | 3.3 * | 22.1 * | 6.6 * | 40.9 @ |
| % alkali in alkali + enteric polymer** | NA | NA | NA | NA |
| Inference | Enteric resistance followed by very less and incomplete release in buffer pH 5.5 was observed | Enteric resistance followed by slow and incomplete release in buffer pH 5.5 was observed | Use of Duocoat technology showed drug release at pH 6.2 but showed very slow and incomplete release in pH 5.8 and below. | Use of Duocoat technology showed drug release at pH 5.8 & 6.2 but showed slow and incomplete release in pH 5.5 and below. |

Enteric protection after 2 hrs exposure to 0.1N HCl; * Drug release after 45 mins; @

TABLE 20(a)-continued

Drug release after 30 mins
**% alkali in alkali + enteric polymer =
Quantity of alkaki (gm) in intermediate coat × 100

$$\left[ \begin{array}{l} \text{Qty. of alkali (gm) in intermediate coat +} \\ \text{Qty. of dry enteric polymer (gm) in enteric coat} \end{array} \right]$$

Abbreviation:
BP: Benazepril pellets; SP: Sotalol Pellets; MgO: Magnesium Oxide; MgCO3:
Magnesium Carbonate; CaO: Calcium Oxide; CaCO3: Calcium Carbonate; TEC:
Triethyl Citrate; Qty.: Quantity; gm: Grams

| Experiment No. | C5 | C6 | C7 |
|---|---|---|---|
| Objective | Alkali control (Coating without alkali in inner layer) | Experiment with very low alkali concentration in inner layer keeping intermediate layer thickness constant | Comparative example similar to example 1 of US 2005214371A1 using pantoprazole as API instead of lansoprazole |
| Core | BP | BP | PP |
| Inner layer (Seal coat) | . . . | . . . | 1.7% w/w HPMC 6 cps + Talc (146.25%) |
| Inner layer (Intermediate coat) | 10% w/w EUDRAGIT L 100 neutralized to pH 7 + Glycerol (25%) + Talc (50%) coating | 10% w/w HPMC + Glycerol (25%) + MgO (10%) | 3.16% w/w HPMC 6 cps + Magnesium Carbonate (150%) |
| Outer layer (Enteric coat) | 15% w/w EUDRAGIT L30D-55 + TEC (10%) +Talc (50%) | 20% w/w EUDRAGIT L30D-55 + TEC (10%) +Talc (50%) | 20% w/w EUDRAGIT L30D-55 + TEC (9.5%) + Talc (42%) + TiO2 (4.75%) |
| | | Dissolution testing in acid media | |
| Enteric protection # | Pass | Pass | Pass |
| | | Dissolution testing in buffer media of respective pH | |
| pH 5.5 | 15.3 * (Fail) | 7.1* | 26.29* |
| pH 4.5 | | 6.8* | |
| pH 3.0 | | 7.8* | |
| % alkali in alkali + enteric polymer** | NA | 4.22% w/w | 18.02% w/w |
| Inference | Enteric resistance followed by very slow and incomplete drug release in buffer pH 5.5 is observed which suggests that alkali in inner layer is required for fast drug release at lower pH | Use of 10% Magnesium oxide (w.r.t. dry binder quantity in intermediate coat) shows enteric resistance followed by less than 10% release in pH buffer 5.5 and lower pH | Slow and incomplete drug release is obtained with comparative example similar to example 1 of US2005214371A1 using pantoprazole as API instead of lansoprazole |

Enteric protection after 2 hrs exposure to 0.1N HCl; * Drug release after 45 mins;
**% alkali in alkali + enteric polymer =
Quantity of alkaki (gm) in intermediate coat × 100

$$\left[ \begin{array}{l} \text{Qty. of alkali (gm) in intermediate coat +} \\ \text{Qty. of dry enteric polymer (gm) in enteric coat} \end{array} \right]$$

Abbreviation:
BP: Benazepril pellets; PP: Pantoprazole Pellets; MgO: Magnesium Oxide; MgCO3:
Magnesium Carbonate; CaO: Calcium Oxide; CaCO3: Calcium Carbonate; Qty.:
Quantity; gm: Grams

The invention claimed is:

1. A dosage form, comprising:
a core, comprising a biologically active ingredient which is stable to a degree of at least 95% at a pH of 3 for 2 hours at 22° C.,
an intermediate coating layer (ICL) onto or above the core, comprising an alkaline agent, and
an enteric coating layer (ECL) onto or above the ICL, comprising an enteric polymer,
wherein a relation in percent of the alkaline agent in the ICL to the enteric polymer in the ECL is 5 to 95% when calculated by the formula:

$$\frac{\text{quantity of the alkaline agent in grams in the } ICL \times 100}{\begin{array}{c}(\text{quantity of the alkaline agent in grams in the } ICL + \\ \text{quantity of the enteric polymer in grams in the } ECL)\end{array}},$$

wherein the alkaline agent is selected from the group consisting of calcium oxide, calcium carbonate, magnesium carbonate, magnesium oxide, sodium carbonate, sodium bicarbonate, sodium hydroxide, and a combination thereof,
wherein the enteric polymer in the ECL is selected from the group consisting of an anionic (meth)acrylate copolymer, an anionic cellulose, an anionic polysaccharide, a polyvinyl acetate phthalate, and a mixture thereof, and
wherein the biologically active ingredient does not comprise lansoprazole.

2. The dosage form according to claim 1, wherein the core comprises the biologically active ingredient distributed in a matrix structure or bound in a binder in a coating on the core.

3. The dosage form according to claim 1, wherein the biologically active ingredient is selected from the group consisting of acetyl salicylic acid, benazepril, bisascodyl, budesonide, carvediol, etopside, quinidine, ketoconazole, sotalol, an enzyme, a hormone, a liquid natural extract, a solid natural extract, an oligonucleotide, DNA, RNA, mRNA, siRNA, Protacs a peptide hormone, therapeutic bacteria, a prebiotic, a probiotic, a peptide, a protein, an omega-3-fatty acid, a salt of an omega-3-fatty acid, an anthocyanine, a vitamin, and a vaccine.

4. The dosage form according to claim 1, wherein the alkaline agent is magnesium oxide.

5. The dosage form according to claim 1, wherein the alkaline agent is magnesium oxide or magnesium carbonate.

6. The dosage form according to claim 1, wherein the ICL further comprises a plasticizer, a polymeric binder, or both.

7. The dosage form according to claim 1, wherein the enteric polymer in the ECL is an anionic (meth)acrylate copolymer.

8. The dosage form according to claim 1, wherein the enteric polymer is an anionic (meth)acrylate copolymer selected from the group consisting of a copolymer comprising polymerized units of methacrylic acid and ethyl acrylate, a copolymer comprising polymerized units of methacrylic acid and methyl methacrylate, a copolymer comprising polymerized units of methacrylic acid, methyl acrylate, and methyl methacrylate, and a mixture thereof.

9. The dosage form according to claim 1, wherein the enteric polymer is an anionic cellulose selected from the group consisting of carboxymethyl ethyl cellulose, a salt of carboxymethyl ethyl cellulose, cellulose acetate phthalate, cellulose acetate succinate, cellulose acetate trimellitate, hydroxypropyl methyl cellulose phthalate, hydroxypropyl methyl cellulose acetate succinate, and a mixture thereof.

10. The dosage form according to claim 1, wherein the biologically active ingredient is released in an amount of 10% or less at a pH of 1.2 for 120 min, and in an amount of 40% or more at a pH from 3 to 5.5 for 45 min.

11. The dosage form according to claim 1, wherein the biologically active ingredient is stable to degradation to a degree of at least 95% for 2 hours at 22° C. at any pH in a pH range from 3.0 to 7.0.

12. The dosage form according to claim 1, wherein the biologically active ingredient which is stable to a degree of at least 95% at a pH of 3 for 2 hours at 22° C., has such stability determined in an assay which is a thin-layer chromatographic identification test, a spectrometric identification test, a nuclear magnetic resonance spectroscopy, a near-infrared spectroscopy, or a Raman spectroscopy.

13. The dosage form according to claim 1, wherein the biologically active ingredient is stable to a degree of at least 95% at a pH of 3.0 for 2 hours at 22° C. in a buffered medium of 0.25 M disodium hydrogen phosphate anhydrous ($Na_2HPO_4$) aqueous solution adjusted to a pH of 3.0 with ortho-phosphoric acid.

14. The dosage form according to claim 1, wherein the relation in percent of the alkaline agent in the ICL to the enteric polymer in the ECL is 7 to 80%.

15. The dosage form according to claim 3, wherein the biologically active ingredient is bilberries, blueberries, or black currants.

16. The dosage form according to claim 1, wherein the biologically active ingredient comprises benazepril.

17. A dosage form, comprising:
a core, comprising a biologically active ingredient which is stable to a degree of at least 95% at a pH of 3 for 2 hours at 22° C.,
an intermediate coating layer (ICL) onto or above the core, comprising an alkaline agent, and
an enteric coating layer (ECL) onto or above the ICL, comprising an enteric polymer,
wherein a relation in percent of the alkaline agent in the ICL to the enteric polymer in the ECL is 5 to 95% when calculated by the formula:

$$\frac{\text{quantity of the alkaline agent in grams in the } ICL \times 100}{\begin{array}{c}(\text{quantity of the alkaline agent in grams in the } ICL + \\ \text{quantity of the enteric polymer in grams in the } ECL)\end{array}},$$

wherein the alkaline agent is selected from the group consisting of calcium oxide, calcium carbonate, magnesium carbonate, magnesium oxide, sodium carbonate, sodium bicarbonate, sodium hydroxide, and a combination thereof, and
wherein the enteric polymer in the ECL is selected from the group consisting of an anionic (meth)acrylate copolymer, an anionic cellulose, an anionic polysaccharide, a polyvinyl acetate phthalate, and a mixture thereof,
wherein the biologically active ingredients in the core consists only of active ingredients which are stable to a degree of at least 95% at a pH of 3 for 2 hours at 22° C.

18. The dosage form according to claim 1, wherein the biologically active ingredients in the core do not contain ingredients which are not stable to a degree of at least 95% at a pH of 3 for 2 hours at 22° C.

19. The dosage form according to claim 1, wherein the biologically active ingredient excludes acid labile drugs.

\* \* \* \* \*